United States Patent
Boyle et al.

(10) Patent No.: US 8,461,339 B2
(45) Date of Patent: Jun. 11, 2013

(54) PHARMACEUTICAL COMPOUNDS

(75) Inventors: Robert George Boyle, Cambridge (GB); David Winter Walker, Linton (GB)

(73) Assignee: Sentinel Oncology Limited, Cambridge, MA (US)

( * ) Notice: Subject to any disclaimer, the term of this patent is extended or adjusted under 35 U.S.C. 154(b) by 191 days.

(21) Appl. No.: 13/003,945

(22) PCT Filed: Jul. 15, 2009

(86) PCT No.: PCT/GB2009/001759
§ 371 (c)(1),
(2), (4) Date: Jan. 13, 2011

(87) PCT Pub. No.: WO2010/007374
PCT Pub. Date: Jan. 21, 2010

(65) Prior Publication Data
US 2011/0130394 A1    Jun. 2, 2011

(30) Foreign Application Priority Data
Jul. 15, 2008    (GB) .................................... 0812969.4

(51) Int. Cl.
*C07D 215/38*    (2006.01)
(52) U.S. Cl.
USPC .......................................... 546/159; 514/313
(58) Field of Classification Search
USPC .......................................... 546/159; 514/313
See application file for complete search history.

(56) References Cited

U.S. PATENT DOCUMENTS

| 7,928,103 | B2 * | 4/2011 | Riether et al. ............. 514/235.5 |
| 2006/0009460 | A1 | 1/2006 | Dickson, Jr. et al. |
| 2010/0029644 | A1 | 2/2010 | Reither et al. |

FOREIGN PATENT DOCUMENTS

| EP | 1854793 A | 11/2007 |
| WO | 99/17759 A2 | 4/1999 |
| WO | 00/50391 A1 | 8/2000 |
| WO | 02/059122 A1 | 8/2002 |
| WO | 2004/058762 A1 | 7/2004 |
| WO | 2004/065378 A1 | 8/2004 |
| WO | 2004/080463 A1 | 9/2004 |
| WO | 2004/098607 A1 | 11/2004 |
| WO | 2005/028444 A1 | 3/2005 |
| WO | 2005/051387 A1 | 6/2005 |
| WO | 2005/100349 A2 | 10/2005 |
| WO | 2005100349 A | 10/2005 |
| WO | 2006/076593 A1 | 7/2006 |
| WO | 2006/114180 A1 | 11/2006 |
| WO | 2007/000240 A1 | 1/2007 |
| WO | 2007000240 A | 1/2007 |
| WO | 2007/125405 A2 | 11/2007 |
| WO | 2008/048914 A1 | 4/2008 |
| WO | 2008048914 A | 4/2008 |

OTHER PUBLICATIONS

International Search Report and Written Opinion for PCT/GB2009/001759.
UK IPO Search Report for GB0812969.4 (priority document for present application) dated Nov. 12, 2008.

\* cited by examiner

*Primary Examiner* — D M Seaman
(74) *Attorney, Agent, or Firm* — Heslin Rothenberg Farley & Mesiti P.C.

(57)    ABSTRACT

The invention provides kinase inhibitor compounds of the formula (1):

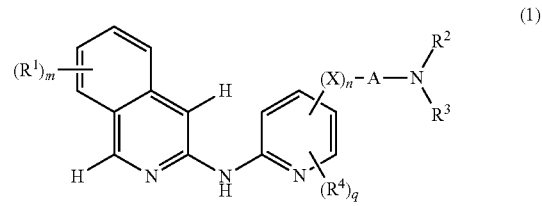

or salts, solvates, tautomers or N-oxides thereof; wherein X is O, CO, $X^1C(X^2)$, $C(X^2)X^1$, $X^1C(X^2)X^1$, S, SO, $SO_2$, $NR^c$, $SO_2NR^c$ or $NR^cSO_2$; m is 0-2; n is 0-1; q is 0-2; A is $C_{1-6}$ alkylene optionally interrupted by O; $R^1$ is halogen, cyano, nitro, an optionally substituted acyclic $C_{1-6}$ hydrocarbon group, optionally substituted $C_{3-7}$ cycloalkyl, optionally substituted phenyl, optionally substituted five membered heteroaryl, $NR^2R^3$, $R^a$—$R^b$, O—$R^b$ or $C(O)NR^2R^8$; $R^4$ is fluorine, chlorine, methyl or cyano; $R^2$ is hydrogen or optionally substituted $C_{1-4}$ alkyl; $R^3$ is $R^a$—$R^b$; or $NR^2R^3$ forms a 4 to 7 membered non-aromatic heterocyclic ring; $R^a$ is a bond, $C(X^2)$, $C(X^2)X^1$, SO, $SO_2$ or $SO_2NR^c$; $R^b$ is hydrogen or an optionally substituted 3 to 7-membered carbocyclic or heterocyclic ring or an optionally substituted $C_{1-12}$ acyclic hydrocarbon group; $R^c$ is hydrogen or a $C_{1-4}$ hydrocarbon group; $R^d$ is O, CO, $X^1C(X^2)$, $C(X^2)X^1$, $X^1C(X^2)X^1$, S, SO, $SO_2$, $NR^c$, $SO_2NR^c$ or $NR^cSO_2$; $X^1$ is O, S or $NR^c$; $X^2$ is =O, =S or =$NR^c$; but excluding the compound wherein m, n and q are all 0, A is $CH_2$ and $NR^2R^3$ is a 2-phenylmorpholin-4-yl group.

17 Claims, No Drawings

PHARMACEUTICAL COMPOUNDS

CROSS REFERENCE TO RELATED APPLICATIONS

This application is a national stage filing under section 371 of International Application No. PCT/GB2009/001759, filed on Jul. 15, 2009, and published in English on Jan. 21, 2010 as WO 2010/007374 A1 and claims priority of Great Britain Application No. 0812969.4 filed on Jul. 15, 2008, the entire disclosure of these applications being hereby incorporated herein by reference.

This invention relates to pyridylamino-isoquinoline compounds having kinase inhibiting activity, the use of the compounds in medicine, pharmaceutical compositions containing the compounds and methods for making them

BACKGROUND OF THE INVENTION

Protein kinases constitute a large family of structurally related enzymes that are responsible for the control of a wide variety of signal transduction processes within the cell (Hardie, G. and Hanks, S. (1995) The Protein Kinase Facts Book. I and II, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., FASEB J., 9:576-596 (1995); Knighton, et al., Science, 253:407-414 (1991); Hiles, et al., Cell, 70:419-429 (1992); Kunz, et al., Cell, 73:585-596 (1993); Garcia-Bustos, et al., EMBO J., 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

Aurora A Kinase

The Aurora kinases are a family of serine/threonine protein kinases critical for the proper regulation of mitosis. Of the three mammalian aurora paralogues, A, B and C, Aurora A and B are commonly overexpressed in human tumours. Aurora A is amplified in many human tumours and is involved in centrosome duplication, bipolar mitotic spindle formation, chromosome alignment and spindle checkpoint.

Yes Kinases

Yes is a member of the Src family of non-receptor tyrosine kinases. Like Src, Yes amplifies signals generated by various receptors, in many cases duplicating the functionality of Src. Expression of Yes is elevated in melanocytes and in melanoma cells, and Yes kinase activity is stimulated by neurotrophins, which are mitogenic and metastatic factors for melanoma cells. In addition to melanoma, yes is also overexpressed in colon cancer.

Abl Kinases

Abl is a non-receptor tyrosine kinase distinguished by its localization in the nucleus as well as the cytoplasm. Cytoplasmic Abl associates with F-actin and is capable of stimulating cell growth. Nuclear Abl is thought to participate with DNA-PK and ATM to initiate signalling in response to DNA damage. Chromosomal translocations involving Abl and the breakpoint cluster region on chromosome 22 produce the bcr-Abl fusion protein, resulting in a constitutively active Abl thought to be critical in the pathogenesis of chronic myelogenous leukemia (CML).

cSRC Kinases c-Src is a non-receptor tryosine kinase belonging to a family including c-Src, c-Yes and Fyn. It is expressed in most cell types at low levels and is activated by dephosphorylation of the Tyr530 site and phosphorylation of a second site, Tyr416, present within the kinase domain. The c-Src oncogene has been implicated in the development of growth, progression and metastasis in a variety of human cancers.

Vascular Endothelial Growth Factor (VEGF)

Vascular endothelial growth factor (VEGF) has a pivotal role in stimulating the pathological angiogenesis required for a number of diseases including cancer. Its expression has been shown to be up-regulated in a variety of tumours and has been reported to be a prognostic indicator of tumour progression and/or decreased survival. VEGF induces a signalling response by binding to VEGF receptor-1 (Flt-1), VEGF receptor-2 (KDR/Flk-1) and VEGF-3 (Flt4).

Activation of the VEGF receptor-2 is considered to be the prominent mechanism by which VEGF induces endothelial cell proliferation and migration.

The functions of VEGF-C and VEGF-D and their receptor Flt4 have been implicated in the onset and promotion of tumour cell metastasis in colorectal cancer (Hebei Yixue (2007), 13(10), 1135-1140); in the metastasis of primary breast cancer (Dalian Yike Daxue Xuebao (2005), 27(6), 413-417) and in lymphatic metastasis in patients with lung cancer (Zhongguo Yike Daxue Xuebao (2005), 34(3), 244-245).

FLT3 Kinase

The ligand for the FMS-like tyrosine kinase 3 (FLT3) receptor is an early acting growth factor in tumour growth events and supports survival, proliferation and differentiation of primitive hemopoietic progenitor cells. Signalling through the FLT3 receptor activates several downstream signalling pathways such as RAS/Raf/MAPK and PI3 kinase cascades (see Takahashi, S. et. al.; Leukemia Research, 29(8), 893-899, 2005. Namikawa, R. et. al.; Stem Cells, 14, 388-395, 1996).

Mutations in the FLT3 gene are amongst the most frequent genetic defects found in acute myeloid leukemia (AML) (see Kottaridis, P. D.; Gale, R. E.; Langabeer, S. E.; Frew, M. E.; Bowen, D. T., Linch; D. C.; Blood, 2002).

Most mutations lead to a constitutively activated receptor which gives rise to an oncogenic nature. Major mutations are length mutations (FLT3-LM also called FLT3-ITD) and tyrosine kinase domain mutations (FLT3-TKD) (see Kiyoi, H.; Chno, R. et. al.; Oncogene, 21(16) 2555-2565, 2002. Yamamoto, Y.; Kiyoi, H.; Blood, 97(8), 2434, 2439, 2001). The latter has been suggested to trigger both activation loop and stabilisation of the active site.

Inhibitors of FLT3 are therefore expected to be of benefit to patients suffering from AML and to inhibit the early angiogenesis events associated with tumour growth and metastasis.

FLT4 Kinase

FMS-like tyrosine kinase 4 (FLT4) is a Vascular endothelial growth factor (VEGF) receptor which is activated by both VEGF-C & VEGF-D. Both of these growth factors have been shown to induce lymphangiogenesis via FLT-4 (see Schneider, M.; Buchler, P.; Giese, N.; Wilting, J.; Buchler, M. W.; Friess, H.; Int. J. Oncol., 2006, 28: 883-890) and have also both been shown to be lymphangiogenic in tumours, stimulating metastasis.

Recent research (see Alitalo, K. et. al.; Cancer Cell, 2008 13, 554-556 and Alitalo, K. et. al.; Nature, 2008 454, 656-660) has shown that targeting inhibitors towards the FLT-4 receptor may provide additional efficacy for anti-angiogenic therapies, especially towards vessels that are resistant to VEGF or VEGFR-2 inhibitors.

Trk Kinases

The Trk family of receptor tyrosine kinases include Trk A, Trk B, and Trk C. Trk A is the high-affinity receptor for NGF, while Trk B is the high-affinity BDNF receptor, and Trk C serves as a receptor for neurotrophin-3 (NT-3). The signalling activity of these receptors includes the Ras, MAP kinase pathway, and the PI3-kinase pathway. It is envisaged that inhibitors of Trk kinases such as Trk A will be useful in cancer therapy.

WO2008/048914 discloses as modulators of the cannabinoid CB2 receptor a class of pyridylaminoisoquinoline compounds.

SUMMARY OF THE INVENTION

In a first aspect, the invention provides a compound of the formula (1):

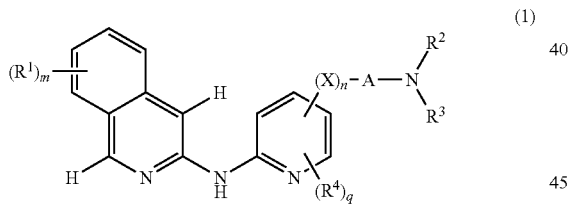

or a salt, solvate, tautomer or N-oxide thereof; wherein

X is O, CO, $X^1C(X^2)$, $C(X^2)X^1$, $X^1C(X^2)X^1$, S, SO, $SO_2$, $NR^c$, $SO_2NR^c$ or $NRS^cSO_2$;

m is 0, 1 or 2;

n is 0 or 1;

q is 0, 1 or 2;

A is a straight chain or branched $C_{1-6}$ alkylene group optionally interrupted by O, provided that when n is 1 and X is O, S or $NR^c$, then there are at least two carbon atoms between X and $NR^2R^3$;

$R^1$ is selected from halogen; cyano; nitro; an acyclic $C_{1-6}$ hydrocarbon group optionally substituted by hydroxy or $C_{1-2}$-alkoxy or by one or more fluorine atoms; $C_{3-7}$ cycloalkyl optionally substituted by one or two substituents selected from amino, hydroxy, fluorine, methoxy and methyl; phenyl optionally substituted by one to three substituents $R^7$; five membered heteroaryl groups containing 1-4 heteroatoms selected from O, N and S, and being optionally substituted by one to three substituents $R^7$; a group $NR^2R^3$; a group $R^a$—$R^b$; a group O—$R^b$; and a group $C(O)NR^2R^8$;

$R^4$ is selected from fluorine, chlorine, methyl or cyano;

$R^2$ is selected from hydrogen and $C_{1-4}$ alkyl optionally substituted by hydroxy, $C_{1-2}$ alkoxy, amino, mono- or di-$C_{1-2}$ alkylamino, $R^3$ is a group $R^a$—$R^b$;

or $NR^2R^3$ forms a 4 to 7 membered non-aromatic heterocyclic ring optionally containing a second heteroatom ring member selected from O, N and S and oxidised forms thereof and being optionally substituted by one or more substituents $R^5$;

$R^a$ is a bond, $C(X^2)$, $C(X^2)X^1$, SO, $SO_2$ or $SO_2NR^c$;

$R^b$ is:

hydrogen; or a 3 to 7-membered carbocyclic or heterocyclic ring containing up to 4 heteroatoms selected from O, N and S and being optionally substituted by one or more substituents $R^5$; or a $C_{1-12}$ acyclic hydrocarbon group optionally substituted by one or more substituents selected from hydroxy; oxo; halogen; cyano; nitro; carboxy; amino; $N(R^c)_2$; and 3 to 7-membered carbocyclic or heterocyclic rings containing up to 4 heteroatoms selected from O, N and S and being optionally substituted by one or more substituents $R^5$; and wherein the $C_{1-12}$ acyclic hydrocarbon group may optionally be interrupted by one or two moieties $R^d$;

$R^c$ is hydrogen or a $C_{1-4}$ hydrocarbon group;

$R^d$ is O, CO, $X^1C(X^2)$, $C(X^2)X^1$, $X^1C(X^2)X^1$, S, SO, $SO_2$, $NR^c$, $SO_2NR^c$ or $NR^cSO_2$;

$X^1$ is O, S or $NR^c$;

$X^2$ is =O, =S or =$NR^c$;

$R^5$ is $X^2$; halogen; cyano; nitro; a group $R^d$—$R^e$; or a 3 to 7-membered carbocyclic or heterocyclic ring containing up to 4 heteroatoms selected from O, N and S and being optionally substituted by a group $R^6$;

$R^e$ is:

hydrogen; or a $C_{1-6}$ acyclic hydrocarbon group optionally substituted by one or more substituents selected from hydroxy; oxo; halogen; cyano; nitro; carboxy; amino; and $N(R^c)_2$; wherein the $C_{1-12}$ acyclic hydrocarbon group may optionally be interrupted by one or moieties $R^d$; or a 3 to 7-membered carbocyclic or heterocyclic ring containing up to 4 heteroatoms selected from O, N and S and being optionally substituted by a group $R^6$; and $R^6$ is selected from halogen, cyano, nitro and a group $R^d$—$R^c$;

$R^7$ is selected from halogen; cyano; $C_{1-4}$ alkoxy optionally substituted with one or more fluorine atoms; $C_{1-4}$ alkyl optionally substituted with hydroxy or $C_{1-2}$-alkoxy or with one or more fluorine atoms; and $C_{3-5}$ cycloalkyl; and $R^8$ is $R^b$; or $NR^2R^8$ forms a 4 to 7 membered non-aromatic heterocyclic ring optionally containing a second heteroatom ring member selected from O, N and S and oxidised forms thereof and being optionally substituted by one or more substituents $R^5$;

but excluding the compound wherein m, n and q are all 0, A is $CH_2$ and $NR^2R^3$ is a 2-phenylmorpholin-4-yl group.

In one embodiment within formula (1), the invention provides a compound of the formula (1a):

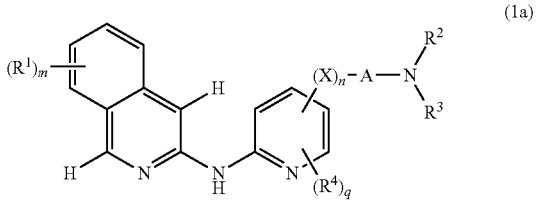

(1a)

or a salt, solvate, tautomer or N-oxide thereof; wherein
X is O, CO, $X^1C(X^2)$, $C(X^2)X^1$, $X^1C(X^2)X^1$, S, SO, $SO_2$, $NR^c$, $SO_2NR^c$ or $NR^cSO_2$;
m is 0, 1 or 2;
n is 0 or 1;
q is 0, 1 or 2;
A is a straight chain or branched $C_{1-6}$ alkylene group optionally interrupted by O, provided that when n is 1 and X is O, S or $NR^c$, then there are at least two carbon atoms between X and $NR^2R^3$;
$R^1$ is selected from halogen; cyano; $C_{1-4}$ alkoxy optionally substituted by one or more fluorine atoms; $C_{1-4}$ alkyl optionally substituted by hydroxy or $C_{1-2}$-alkoxy or by one or more fluorine atoms; $C_{3-5}$ cycloalkyl; phenyl optionally substituted by one to three substituents $R^7$; five membered heteroaryl groups containing 1-4 heteroatoms selected from O, N and S, and being optionally substituted by one to three substituents $R^7$;
$R^4$ is selected from fluorine, chlorine, methyl or cyano;
$R^2$ is selected from hydrogen and $C_{1-4}$ alkyl optionally substituted by hydroxy, $C_{1-2}$ alkoxy, amino, mono- or di-$C_{1-2}$ alkylamino,
$R^3$ is a group $R^a$—$R^b$;
or $NR^2R^3$ forms a 4 to 7 membered non-aromatic heterocyclic ring optionally containing a second heteroatom ring member selected from O, N and S and oxidised forms thereof and being optionally substituted by one or more substituents $R^5$;
$R^a$ is a bond, $C(X^2)$, $C(X^2)X^1$, SO, $SO_2$ or $SO_2NR^c$;
$R^b$ is:
hydrogen; or
a 3 to 7-membered carbocyclic or heterocyclic ring containing up to 4 heteroatoms selected from O, N and S and being optionally substituted by one or more substituents $R^5$; or
a $C_{1-12}$ acyclic hydrocarbon group optionally substituted by one or more substituents selected from hydroxy; oxo; halogen; cyano; nitro; carboxy; amino; $N(R^c)_2$; and 3 to 7-membered carbocyclic or heterocyclic rings containing up to 4 heteroatoms selected from O, N and S and being optionally substituted by one or more substituents $R^5$; and wherein the $C_{1-12}$ acyclic hydrocarbon group may optionally be interrupted by one or two moieties $R^d$;
$R^c$ is hydrogen or a $C_{1-4}$ hydrocarbon group;
$R^d$ is O, CO, $X^1C(X^2)$, $C(X^2)X^1$, $X^1C(X^2)X^1$, S, SO, $SO_2$, $NR^c$, $SO_2NR^c$ or $NR^cSO_2$;
$X^1$ is O, S or $NR^c$;
$X^2$ is =O, =S or =$NR^c$;
$R^5$ is $X^2$; halogen; cyano; nitro; a group $R^d$—$R^e$; or a 3 to 7-membered carbocyclic or heterocyclic ring containing up to 4 heteroatoms selected from O, N and S and being optionally substituted by a group $R^6$;
$R^e$ is:
hydrogen; or
a $C_{1-6}$ acyclic hydrocarbon group optionally substituted by one or more substituents selected from hydroxy; oxo; halogen; cyano; nitro; carboxy; amino; and $N(R^c)_2$; wherein the $C_{1-12}$ acyclic hydrocarbon group may optionally be interrupted by one or moieties $R^d$; or
a 3 to 7-membered carbocyclic or heterocyclic ring containing up to 4 heteroatoms selected from O, N and S and being optionally substituted by a group $R^6$; and
$R^6$ is selected from halogen, cyano, nitro and a group $R^d$—$R^c$; and
$R^7$ is selected from halogen; cyano; $C_{1-4}$ alkoxy optionally substituted with one or more fluorine atoms; $C_{1-4}$ alkyl optionally substituted with hydroxy or $C_{1-2}$-alkoxy or with one or more fluorine atoms; and $C_{3-5}$ cycloalkyl;
but excluding the compound wherein m, n and q are all 0, A is $CH_2$ and $NR^2R^3$ is a 2-phenylmorpholin-4-yl group.

In formulae (1) and (1a), X is O, CO, $X^1C(X^2)$, $C(X^2)X^1$, $X^1C(X^2)X^1$, S, SO, $SO_2$, $NR^c$, $SO_2NR^c$ or $NR^cSO_2$ and n is 0 or 1. In a preferred group of compounds within each of formulae (1) and (1a), n is 1 and X is O. In another preferred group within each of formulae (1) and (1a) of compounds, n is 0.

The following embodiments, preferences and examples are applicable to each of formulae (1) and (1a) unless the context indicates otherwise.

A is a straight chain or branched $C_{1-6}$ alkylene group optionally interrupted by O, provided that when n is 1 and X is O, S or $NR^c$, then there are at least two carbon atoms between X and $NR^2R^3$. Examples of alkylene groups $C_1$, $C_2$, $C_3$, $C_4$ and $C_5$ alkylene groups. One preferred subgroup of alkylene groups consists of $C_1$, $C_2$, $C_3$ and $C_4$ alkylene groups.

When n is 0, A can be, for example, —$CH_2$—, —$CH_2CH_2$—, —$CH_2CH_2CH_2$— or —$CH_2CH_2CH_2CH_2$—. When n is 1 and X is O, S or $NR^c$, A can be, for example, —$CH_2CH_2$—, —$CH_2CH_2CH_2$— or —$CH_2CH_2CH_2CH_2$—, and more preferably is —$CH_2CH_2$— or —$CH_2CH_2CH_2$—.

When n is 0 and A is a straight chain or branched $C_{1-6}$ alkylene group interrupted by O, A can be, for example, selected from —$CH_2$—O—$CH_2CH_2$—, —$CH_2CH_2$—O—$CH_2CH_2$—, —$CH_2$—O —$CH_2CH_2$— and —$CH_2CH_2$—O—$CH_2CH_2CH_2$—.

When n is 1 and X is O, S or $NR^c$, and A is a straight chain or branched $C_{1-6}$ alkylene group interrupted by O, then A can be, for example, selected from —$CH_2CH_2$—O—$CH_2CH_2$— and —$CH_2CH_2$—O—$CH_2CH_2$ $CH_2$—.

The integer m is 0, 1 or 2. More preferably m is 0 or 1. In one sub-group of compounds, m is 0. In another subgroup of compounds, m is 1.

In formula (1), $R^1$ is selected from halogen; cyano; nitro; an acyclic $C_{1-6}$ hydrocarbon group optionally substituted with hydroxy or $C_{1-2}$-alkoxy or with one or more fluorine atoms; $C_{3-7}$ cycloalkyl optionally substituted by one or two substituents selected from amino, hydroxy, fluorine, methoxy and methyl; phenyl optionally substituted by one to three substituents $R^7$; five membered heteroaryl groups containing 1-4 heteroatoms selected from O, N and S, and being optionally substituted by one to three substituents $R^7$; a group $NR^2R^3$; a group $R^a$—$R^b$; a group O—$R^b$; and a group $C(O)NR^2R^8$.

When $R^1$ is an optionally substituted acyclic $C_{1-6}$ hydrocarbon group, it can be for example an optionally substituted alkyl group (straight chain or branched), an alkenyl group (straight chain or branched); or an alkynyl group.

For example, $R^1$ can be a $C_{1-4}$ alkyl group or a $C_{2-4}$ alkynyl group.

When $R^1$ is a group O—$R^b$, $R^b$ can be for example a $C_{1-4}$ alkyl group optionally substituted with one or more fluorine atoms; or a 4 to 7-membered monocyclic saturated carbocyclic or heterocyclic ring containing up to two heteroatoms selected from O, N and S and being optionally substituted by one or two groups $R^6$.

When $R^1$ is a group a group $NR^2R^3$, it can be for example an amino, mono-$C_{1-4}$alkylamino, di-$C_{1-4}$alkylamino, $C_{1-4}$alkanoylamino, $C_{1-4}$alkylsulphonylamino, ureido, $C_{1-4}$alkylureido or $C_{3-6}$cycloalkylureido group.

When $R^1$ is a group $R^a$—$R^b$, $R^a$ can be for example, C=O, C(O)$NR^c$, SO, $SO_2$, or $SO_2NR^c$, and $R_b$ can be, for example, $C_{1-6}$ alkyl or a saturated 4 to 6-membered carbocyclic or heterocyclic ring containing up to 2 heteroatoms selected from O, N and S and being optionally substituted by one or more $C_{1-6}$ alkyl, $C_{1-6}$ alkanoyl, carbamoyl, mono-N—$C_{1-6}$ alkylcarbamoyl or di-N—$C_{1-6}$ carbamoyl groups.

In formula (1a), $R^1$ is selected from halogen; cyano; $C_{1-4}$ alkoxy optionally substituted with one or more fluorine atoms; $C_{1-4}$ alkyl optionally substituted with hydroxy or $C_{1-2}$-alkoxy or with one or more fluorine atoms; $C_{3-5}$ cycloalkyl; phenyl optionally substituted by one to three substituents $R^7$; five membered heteroaryl groups containing 1-4 heteroatoms selected from O, N and S, and being optionally substituted by one to three substituents $R^7$; where $R^7$ is selected from halogen; cyano; $C_{1-4}$ alkoxy optionally substituted with one or more fluorine atoms; $C_{1-4}$ alkyl optionally substituted with hydroxy or $C_{1-2}$-alkoxy or with one or more fluorine atoms; and $C_{3-5}$ cycloalkyl.

When $R^1$ is a five membered heteroaryl group, it can, for example, contain one, two or three heteroatoms and more typically one or two heteroatoms. Examples of five membered heteroaryl groups include pyrrole, furan, thiophene, pyrazole, imidazole, oxazole, isoxazole, thiazole, isothiazole and triazole, each optionally substituted as hereinbefore defined. One particular subset of heteroaryl groups consists of optionally substituted imidazole and pyrazole groups.

When $R^1$ is an optionally substituted phenyl group or five membered heteroaryl group, it can be unsubstituted or substituted by one to three substituents $R^7$. In one group of compounds, the phenyl group or five membered heteroaryl group has 0, 1 or 2 substituents. In another group of compounds, the phenyl group or five membered heteroaryl group has 0 or 1 substituents. In one particular embodiment, the phenyl group or five membered heteroaryl group is unsubstituted.

In one sub-group of compounds, $R^1$ is selected from halogen; cyano; $C_{1-4}$ alkoxy optionally substituted with one or more fluorine atoms; $C_{1-4}$ alkyl optionally substituted with hydroxy or $C_{1-2}$-alkoxy or with one or more fluorine atoms; $C_{3-4}$ cycloalkyl; and five membered heteroaryl groups containing 1-4 heteroatoms selected from O, N and S and being optionally substituted with one or two methyl groups or halogen atoms.

More preferably, $R^1$ is selected from chlorine; fluorine; bromine; cyano; $C_{1-3}$ alkyl optionally substituted with hydroxy or methoxy or with one or more fluorine atoms; $C_{1-3}$ alkoxy optionally substituted with one or more fluorine atoms; and five membered heteroaryl groups containing 1-2 heteroatoms selected from O, N and S and being optionally substituted with one or two methyl groups.

In a further embodiment, m is 0 or m is 1 and $R^1$ is selected from chlorine; fluorine; cyano; $C_{1-3}$ alkyl optionally substituted with hydroxy or methoxy or with one or more fluorine atoms; and $C_{1-3}$ alkoxy optionally substituted with one or more fluorine atoms.

$R^4$ is selected from fluorine, chlorine, methyl or cyano and the integer q is selected from 0, 1 or 2. More preferably, q is 0 or 1 and most preferably q is 0.

$R^2$ is selected from hydrogen and $C_{1-4}$ alkyl optionally substituted by hydroxy, $C_{1-2}$ alkoxy, amino, mono- or di-$C_{1-2}$ alkylamino. More particularly, $R^2$ is selected from hydrogen, $C_{1-3}$ alkyl, and $C_{2-3}$ alkyl substituted by amino, mono- or dimethylamino alkylamino. More preferably, $R^2$ is selected from hydrogen, methyl and ethyl.

$R^3$ is a group $R^a$—$R^b$. More particularly, $R^3$ is selected from hydrogen and $C_{1-4}$ alkyl optionally substituted by hydroxy, $C_{1-2}$ alkoxy, amino, mono- or di-$C_{1-2}$ alkylamino. Preferably, $R^3$ is selected from hydrogen, $C_{1-3}$ alkyl, and $C_{2-3}$ alkyl substituted by amino, mono- or dimethylamino alkylamino. More preferably, $R^3$ is selected from hydrogen, methyl and ethyl.

Alternatively, $NR^2R^3$ can form a 4 to 7 membered non-aromatic heterocyclic ring optionally containing a second heteroatom ring member selected from O, N and S and oxidised forms thereof and being optionally substituted by one or more substituents $R^5$. Preferred non-aromatic heterocyclic rings are 5 and 6-membered rings and particular examples are pyrrolidine, piperidine, piperazine, morpholine and thiomorpholine, each of which may be optionally substituted with one or more (preferably 0, 1 or 2 and more preferably 0 or 1) substituents $R^5$.

In one particular embodiment, $NR^2R^3$ forms saturated heterocyclic ring selected from pyrrolidine, piperidine and piperazine, the saturated heterocyclic ring being optionally substituted by one or more substituents $R^5$.

$R^5$ is $X^2$; halogen; cyano; nitro; a group $R^d$—$R^e$; or a 3 to 7-membered carbocyclic or heterocyclic ring containing up to 4 heteroatoms selected from O, N and S and being optionally substituted by a group $R^6$.

More typically, $R^5$ is selected from hydroxy, $C_{1-4}$ alkyl; hydroxy-$C_{14}$ alkyl; $C_{1-4}$ alkanoyl; hydroxy-$C_{1-4}$ alkanoyl; $C_{1-4}$ alkylsulphonyl; carbamoyl; mono-$C_{1-4}$ alkylcarbamoyl and di-$C_{1-4}$ alkylcarbamoyl.

Particular examples of $R^5$ are methylsulphonyl, acetyl, carbamoyl, N-methylcarbamoyl, N,N-dimethylcarbamoyl and hydroxyacetyl.

In one preferred embodiment, the invention provides a compound having the general formula (2):

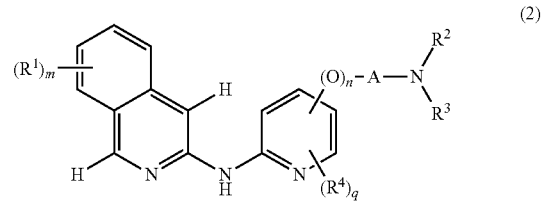

or a salt, solvate, tautomer or N-oxide thereof;

wherein $R^1$, $R^2$, $R^3$, $R^4$, m, n and q are as defined above in respect of formulae (1) and (1a); but excluding the compound wherein m, n and q are all 0, A is $CH_2$ and $NR^2R^3$ is a 2-phenylmorpholin-4-yl group.

In another preferred embodiment, the invention provides a compound having the formula (3):

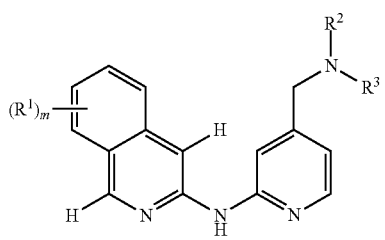

(3)

or a salt, solvate, tautomer or N-oxide thereof;
wherein $R^1$, $R^2$, $R^3$ and m are as defined above in respect of formulae (1) and (1a); excluding the compound wherein m is 0 and $NR^2R^3$ is a 2-phenylmorpholin-4-yl group.

In a further preferred embodiment, the invention provides a compound having the formula (4):

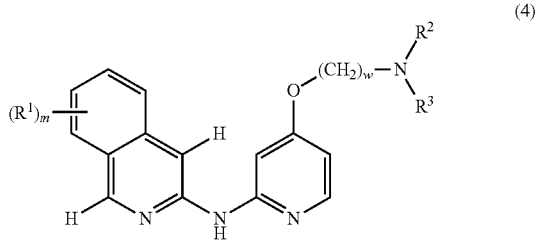

(4)

or a salt, solvate, tautomer or N-oxide thereof;
wherein w is 2 or 3 and $R^1$, $R^2$, $R^3$ and m are as defined above in respect of formulae (1) and (1a).

The above formulae (1), (1a), (2), (3) and (4) each exclude the compound wherein m, n and q are all 0, A is $CH_2$ and $NR^2R^3$ is a 2-phenylmorpholin-4-yl group. The excluded compound is disclosed in example 33 on page 21 of WO2008/048914 and is described as having CB2 receptor modulator activity.

In a more general particular embodiment, the compound of formula (1) (or formula (1a), (2), (3) or (4)) may be other than a compound in which $NR^2R^3$ is a 2-phenylmorpholin-4-yl group.

In a further general embodiment, the compound of formula (1) (or formula (1a), (2), (3) or (4)) may be other than a compound in which $NR^2R^3$ is a 2-phenylmorpholin-4-yl group wherein the 2-phenyl group is unsubstituted or substituted.

The various functional groups and substituents making up a compound of the formulae (1), (1a), (2), (3) and (4) are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Particular and preferred compounds are as set out in the examples.

Salts, Solvates, Tautomers, Isomers, Prodrugs and Isotopes

Unless the context indicates otherwise, a reference to a compound of the formula (1) includes within its scope formulae (1), (1a) (2), (3) or (4) and sub-groups, embodiments and examples thereof, and also includes ionic forms, salts, solvates, isomers, tautomers, prodrugs, isotopes and protected forms thereof, for example, as discussed below.

Many compounds of the formulae (1), (1a), (2), (3) or (4) can exist in the form of salts, for example acid addition salts or, in certain cases salts of organic and inorganic bases such as phenolate, carboxylate, sulphonate and phosphate salts. All such salts are within the scope of this invention, and references to compounds of the formulae (1), (1a), (2), (3) or (4) include the salt forms of the compounds.

The salts can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, non-aqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethane-sulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-aminosalicylic, sebacic, stearic, succinic, sulphuric, tannic, (+)-L-tartaric, thiocyanic, p-toluenesulphonic, undecylenic and valeric acids, as well as acylated amino acids and cation exchange resins.

If the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth metal cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formulae (1), (1a), (2), (3) or (4) may exist in a number of different geometric isomeric, and tautomeric forms and references to compounds of the formulae (1), (1a), (2), (3) or (4) include all such forms. For the avoidance of doubt, where a compound can exist in one of several geometric isomeric or tautomeric forms and only one is specifically described or shown, all others are nevertheless embraced by formulae (1), (1a), (2), (3) or (4).

Examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

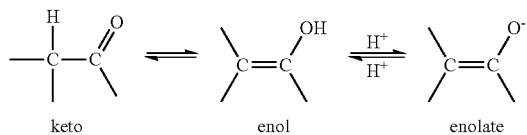

keto    enol    enolate

Where compounds of the formulae (1), (1a), (2), (3) or (4) contain one or more chiral centres, and can exist in the form of two or more optical isomers, references to compounds of the formulae (1), (1a), (2), (3) or (4) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (1), (1a), (2), (3) or (4) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (1), (1a), (2), (3) or (4) having one or more chiral centres, wherein at least 55% (e.g. at least 60%, 65%, 70%, 75%, 80%, 85%, 90% or 95%) of the compound of the formula (1), (1a), (2), (3) or (4) is present as a single optical isomer (e.g. enantiomer or diastereoisomer). In one general embodiment, 99% or more (e.g. substantially all) of the total amount of the compound of the formula (1), (1a), (2), (3) or (4) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Also encompassed by formula (1), (1a), (2), (3) or (4) are any polymorphic forms of the compounds, solvates (e.g. hydrates), complexes (e.g. inclusion complexes or clathrates with compounds such as cyclodextrins, or complexes with metals) of the compounds, and pro-drugs of the compounds.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn et al., *Solid-State Chemistry of Drugs*, Second Edition, published by SSCI, Inc of West Lafayette, Ind., USA, 1999, ISBN 0-967-06710-3.

By "prodrugs" is meant for example any compound that is converted in vivo into a biologically active compound of the formula (1), (1a), (2), (3) or (4).

Methods for the Preparation of Compounds of the Invention

The invention also provides methods for the preparation of compounds of the formula (1), (1a), (2), (3) or (4). In this section, unless the context indicates otherwise, references to formula (1) include any sub-formulae (e.g. (1a), (2), (3) or (4)), sub-groups, embodiments and examples thereof as defined herein.

Accordingly, in another aspect of the invention, there is provided a process for the preparation of a compound of the formula (1), which process comprises the reaction of a compound of the formula (10):

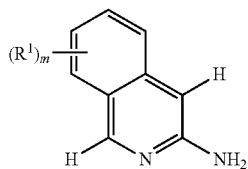

(10)

with a compound of formula (11):

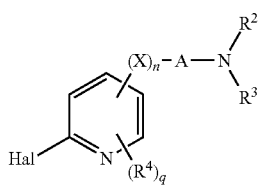

(11)

where $R^1$, $R^2$, $R^3$, $R^4$, X, m, n and q are as defined for formula (1) and Hal is a halogen (preferably chlorine or bromine), in the presence of a palladium (0) catalyst and a base; and thereafter optionally converting one compound of the formula (1) into another compound of the formula (1).

The reaction is typically carried out under Buchwald cross-coupling conditions. Thus, the reaction may be carried out in the presence of a palladium catalyst, for example tris(dibenzylideneacetone)dipalladium(0) ($Pd_2(dba)_3$), together with a further ligand such as 9,9-dimethyl-4,5-bis(diphenylphosphino)-xanthene (Xantphos), a metal carbonate base such as caesium carbonate, and a non-protic solvent such as toluene. Advantageously, the reaction can be performed at an elevated temperature (e.g. approximately 100° C.), for example in a sealed tube.

Compounds of the formula (10) are either known compounds (and may be commercially available) or can be made by methods well known to the skilled person.

For example, compounds of the formula (10) can be prepared following the series of reactions shown in Scheme 1 and described in WO2007125405.

In Scheme 1, the compound of formula (10) is prepared by cyclisation of the substituted N-benzyl-2,2-diethoxyethanimidamide (16) by treatment with sulphuric acid. The reaction may be carried out at room temperature.

The substituted N-benzyl-2,2-diethoxyethanimidamide (16) can be synthesised by the reaction of the methyl 2,2-diethoxyethanimidoate (14) with the optionally substituted benzylamine (15). The reaction is typically carried out in a polar solvent such as an alcohol, e.g. methanol, with heating, for example up to a temperature of about 70-80° C. The methyl 2,2-diethoxyethanimidoate (14) can be prepared by partial methanolysis of the diethoxyacetonitrile (13) using sodium methoxide.

Compounds of the formula (10) where $R^1$ is a five membered heteroaryl group can be prepared from the corresponding compound of formula (10) where $R^1$ is a halogen, and in particular bromine or chlorine, by reaction with a boronate ester or a boronic acid Het-B(OH)$_2$ (where Het is the heteroaryl group) in the presence of a palladium (0) catalyst and base. Boronates suitable for use in preparing compounds of the formula (10) are widely commercially available, for example from Boron Molecular Limited of Noble Park, Australia, or from Combi-Blocks Inc, of San Diego, USA. Where the boronates are not commercially available, they can be prepared by methods known in the art, for example as described in the review article by N. Miyaura and A. Suzuki, Chem. Rev. 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid.

An alternative route to compounds of the formula (10) is shown in Scheme 2.

Scheme 1

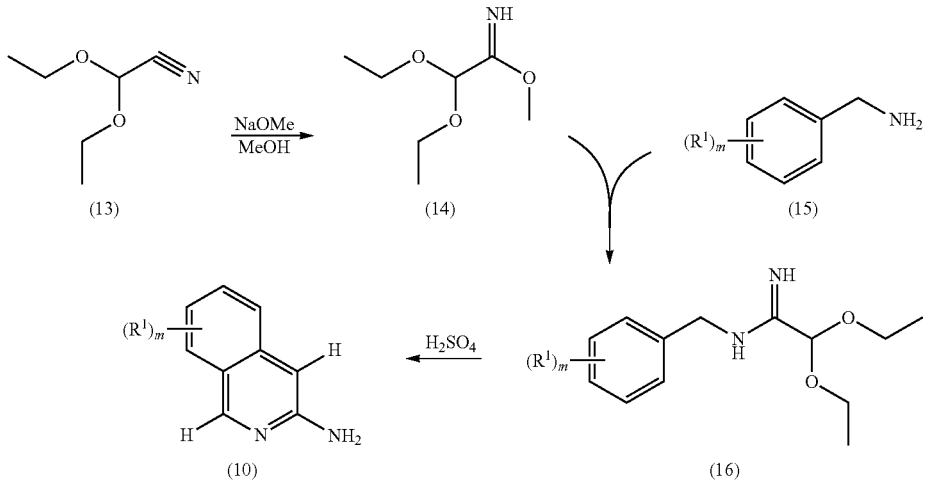

Scheme 2

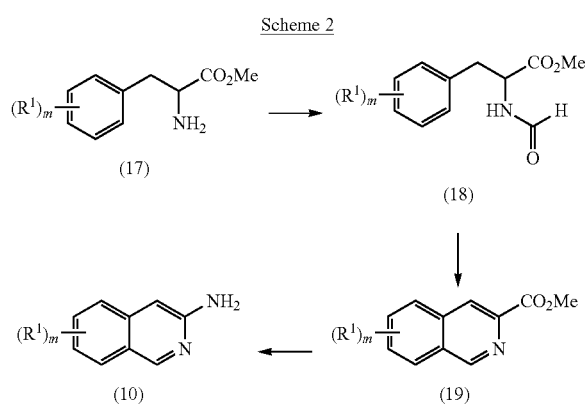

In Scheme 2, the amino group of the amino acid (17) is formylated to give the amido ester (18) using formic acid and a carboxylic acid activating agent such as a substituted carbodiimide, e.g. (1-ethyl-3-[3-dimethylaminopropyl]carbodiimide (EDC or EDAC). The amide coupling reaction may be carried out in a chlorinated solvent such as dichloromethane in the presence of a non-interfering base such as triethylamine or N-methylmorpholine.

The amido ester (18) can be cyclised to the isoquinoline ester (19) by treatment with oxalyl chloride followed by ferric chloride and then heating to reflux with an acid such as sulphuric acid. The isoquinoline ester can then be hydrolysed using potassium hydroxide and the resulting carboxylic acid converted to the azide by acid chloride formation (e.g. using $SOCl_2$ or oxalyl chloride/catalytic DMF) and reaction with sodium azide. Alternatively, the carboxylic acid can be reacted with diphenylphosphoryl azide in the presence of a non-interfering base such as triethylamine in a solvent such as toluene. The azide can then be heated so that it undergoes Curtius rearrangement to form an intermediate isocyanate which is hydrolysed to give the amine (10).

Compounds of the formula (11) can be prepared by a variety of methods.

For example, compounds of the formula (11) can be prepared by the reaction of a compound of the formula (20):

with a compound of the formula $HNR^2R^3$ or a protected form thereof.

The reaction with the compound of the formula $HNR^2R^3$ or protected form thereof may be carried out in a polar solvent such as acetonitrile or DMF, optionally in the presence of another base such as metal carbonate, e.g. potassium carbonate. The reaction may typically be carried out at room temperature.

Compounds of the formula (20) can be prepared by methods well known to the skilled person or methods analogous thereto.

For example, when n is 0 and A is a $CH_2$ group, the compound of formula (20) can be prepared from the corresponding alcohol by treatment with a chlorinating agent such as thionyl chloride. The alcohol in turn can be prepared by reduction of the corresponding carboxylic acid (e.g. a substituted nicotinic acid) using a borane or borohydride reducing agent.

In order to prepare compounds wherein, in formula (1), n is 0 and A is $CH_2$, the corresponding compound of formula (11) can be prepared by the reductive amination of a compound of formula (21):

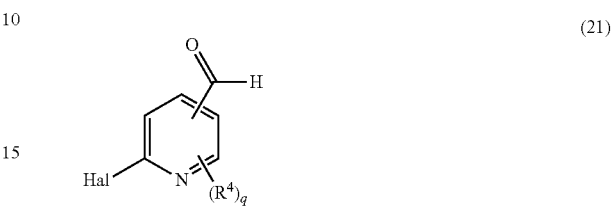

with an amine of the formula $HNR^2R^3$ in the presence of a suitable reducing agent such as sodium triacetoxyborohydride.

Amines of the formula $HNR^2R^3$ are commercially available or can be prepared by methods well known to the skilled person.

Compounds of the formula (11) wherein n is 1 and X is O can be prepared by the reaction of a compound of the formula (22):

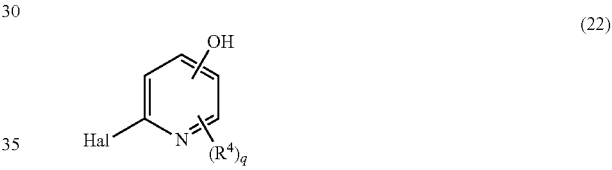

where the hydroxy group is at the 3- or 4-position of the pyridine ring, with a compound of the formula $Br-A-NR^2R^3$ in the presence of a non-nucleophilic base such as an alkali metal hydride (e.g. sodium hydride). The reaction is typically carried out in a polar aprotic solvent such as dimethylformamide, for example at room temperature.

In many of the reactions described above, it may be necessary to protect one or more functional groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

Once formed, one compound of the formula (1) can optionally be converted to another compound of the formula (1) by methods well known to the skilled person or methods analogous thereto, see for example *Fiesers' Reagents for Organic Synthesis*, Volumes 1-17, John Wiley, edited by Mary Fieser (ISBN: 0-471-58283-2), and *Organic Syntheses*, Volumes 1-8, John Wiley, edited by Jeremiah P. Freeman (ISBN: 0-471-31192-8), 1995.

Biological Activity

The compounds of the formula (1) and sub-groups thereof are inhibitors of various kinases such as Flt3, Flt4, Aurora (e.g. Aurora A), KDR, Trk kinases (e.g. Trk A) and Yes kinases, and consequently are expected to be beneficial in preventing or treating a range of diseases in which such kinases are implicated. In particular, the compounds of the formulae (1) and sub-groups thereof are expected to be useful in preventing or treating diseases such as cancers that are characterised by abnormal expression of any of the above kinases or by the involvement of mutant forms of the kinases.

Thus, for example, the compounds of the formula (1) and sub-groups thereof are useful in treating a wide spectrum of proliferative disorders.

Examples of such proliferative disorders include, but are not limited to carcinomas, for example carcinomas of the bladder, breast, colon, kidney, epidermis, liver, lung, oesophagus, gall bladder, ovary, pancreas, stomach, cervix, thyroid, prostate, gastrointestinal system, or skin, haematopoietic tumours such as leukaemia, B-cell lymphoma, T-cell lymphoma, Hodgkin's lymphoma, non-Hodgkin's lymphoma, hairy cell lymphoma, or Burkett's lymphoma; hematopoieitic tumours of myeloid lineage, for example acute and chronic myelogenous leukaemias, myelodysplastic syndrome, or promyelocytic leukaemia; thyroid follicular cancer; tumours of mesenchymal origin, for example fibrosarcoma or habdomyosarcoma; tumours of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; Kaposi's sarcoma or lymphangiogesis.

By virtue of their activity as inhibitors of Flt3 and FLt4, the compounds of the present invention should also be useful in preventing or inhibiting angiogenesis and the development of metastases.

Pharmaceutical Formulations

While it is possible for the active compound to be administered alone, it is preferable to present it as a pharmaceutical composition (e.g. formulation) comprising at least one active compound of the invention together with a pharmaceutically acceptable carrier, and optionally one or more additional excipients.

Accordingly, in another aspect, the invention provides a pharmaceutical composition comprising a compound of the formula (1) and a pharmaceutically acceptable carrier.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris (hydroxymethyl)-aminomethane (TRIS), or carbonate.

The combination of an aqueous solution and a water-soluble organic solvent/surfactant (i.e., a cosolvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively increased water solubility can be achieved through molecular complexation with cyclodextrins.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of Formula (1) or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (1) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known.

For administration by inhalation, the powdered formulations typically comprise the active compound together with an inert solid powdered diluent such as lactose.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient.

The compounds will typically be administered in amounts that are therapeutically or prophylactically useful and which generally are non-toxic. However, in certain situations (for example in the case of life threatening diseases), the benefits of administering a compound of the formula (1) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams) per kilogram of bodyweight although higher or lower doses may be administered where required. Ultimately, the quantity of compound administered and the type of composition used will be commensurate with the nature of the disease or physiological condition being treated and will be at the discretion of the physician.

The compounds of the formula (1) can be administered as the sole therapeutic agent or they can be administered in combination therapy with one of more other compounds for treatment of a particular disease state, for example a cancer as hereinbefore defined. The compounds of the invention may also be administered in conjunction with non-chemotherapeutic treatments such as radiotherapy, photodynamic therapy, surgery and controlled diets.

A person skilled in the art would know through their common general knowledge the dosing regimes and combination therapies to use.

Methods of Diagnosis

Prior to administration of a compound of the formula (1), a patient may be screened to determine whether a disease or condition from which the patient is or may be suffering is one which would be susceptible to treatment with a compound having activity against a particular kinase, for example an Aurora kinase, Flt3 kinase, Flt4 kinase, KDR or Yes kinase.

For example, a biological sample taken from a patient may be analysed to determine whether a condition or disease, such as cancer, that the patient is or may be suffering from is one which is characterised by a genetic abnormality (e.g. mutation) or abnormal protein expression which leads to over-activation (up-regulation) of a particular kinase or to sensitisation of a pathway to normal kinase activity. Thus, for example, the patient may be subjected to a diagnostic test to detect a marker characteristic of up-regulation of a particular kinase. The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine. Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation. In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer, 1987 Meth. Enzymol., 152: 649). Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine. Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies.

The invention will now be illustrated in greater detail by reference to the specific embodiments described in the following non-limiting examples.

EXAMPLES

The invention will now be illustrated in greater detail by reference to the specific embodiments described in the following non-limiting examples.

In the examples, the following abbreviations are used.
DCM dichloromethane
DME dimethoxyethane
DMSO dimethylsulphoxide
dba dibenzylideneacetone
dppf 1,1'-bis(diphenylphosphino)ferrocene
EtOAc ethyl acetate
IPA isopropyl alcohol
MeOH methanol
NMR nuclear magnetic resonance
RT room temperature
h hours
$SiO_2$ silica
TEA triethylamine
THF tetrahydrofuran For compounds other than those described as being prepared by literature methods, NMR and LC/MS data when given were obtained using the conditions set out below.

NMR Conditions

Proton magnetic resonance ($^1$H NMR) spectra were recorded on a Bruker 400 instrument operating at 400 MHz, in DMSO-$d_6$ or MeOH-$d_4$ (as indicated) at 27° C., unless otherwise stated and are reported as follows: chemical shift δ/ppm (number of protons, multiplicity where s=singlet, d=doublet, t=triplet, q=quartet, m=multiplet, br=broad). The residual protic solvent was used as the internal reference.

Liquid chromatography and mass spectroscopy analyses were carried out using the system and operating conditions set out below. Where atoms with different isotopes are present and a single mass quoted, the mass quoted for the compound is the monoisotopic mass (i.e. $^{35}$Cl; $^{79}$Br etc.)

LC/MS Conditions

Samples were analysed by reverse phase HPLC-MS using a Waters 2795 Alliance HT HPLC, a Micromass ZQ mass spectrometer and a Waters 996 photodiode array UV detector. The LC-MS used electrospray ionisation and one of two different chromatography systems, as follows.

Solvents

C=1.58 g ammonium formate in 2.5 L water+2.5 mL Ammonia solution

D=2.5 L Acetonitrile+132 mL (5%) solvent C+2.5 mL Ammonia solution

Chromatography

| Column | Phenomenex Gemini C18, 5 um, 4.6 × 30 mm |
|---|---|
| Injection Volume | 5 μL |
| UV detection | 220 to 400 nm |
| Column Temperature | 35° C. |

| Time | A % | B % | C % | D % | Flow (mL/min) |
|---|---|---|---|---|---|
| 0.00 | 0.0 | 0.0 | 95.0 | 5.0 | 2.000 |
| 4.25 | 0.0 | 0.0 | 5.0 | 95.0 | 2.000 |
| 5.80 | 0.0 | 0.0 | 5.0 | 95.0 | 2.000 |
| 5.90 | 0.0 | 0.0 | 95.0 | 5.0 | 2.000 |
| 7.00 | 0.0 | 0.0 | 95.0 | 5.0 | 2.000 |

Mass Spectrometer

| Ionization mode: | Positive | Negative |
|---|---|---|
| Capillary Voltage: | 3.20 kV | −3.00 kV |
| Cone Voltage: | 30 V | −30 V |
| Source Temperature: | 110° C. | 110° C. |
| Desolvation Temperature: | 350° C. | 350° C. |
| Cone Gas Flow: | 30 L/Hr | 30 L/Hr |
| Desolvation Gas Flow: | 400 L/Hr | 400 L/Hr |
| Scan duration: | 0.50 seconds | 0.50 seconds |
| Interscan delay: | 0.20 seconds | 0.20 seconds |
| Mass range: | 80 to 1000 AMU | 80 to 1000 AMU |

Preparation of Amines of the Formula HNR$^2$R$^3$

Preparation A-1

Piperazine-1-carboxylic acid methylamide

It is envisaged that the title compound will be preparable by the sequence of reactions shown below.

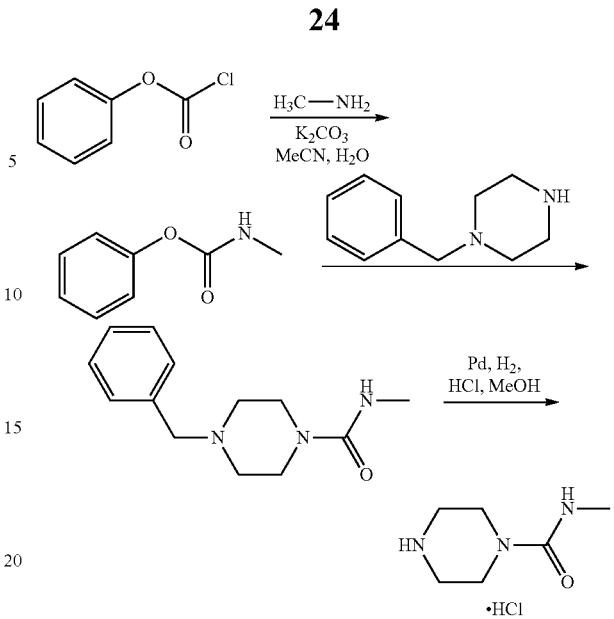

Phenylchloroformate (1 equiv.) is reacted with methylamine (1 equiv.) in acetonitrile:water mixture in the presence of potassium carbonate to give methyl-carbamic acid phenyl ester which then reacted with 1-benzylpiperazine to give 4-benzyl-piperazine-1-carboxylic acid methylamide. The 4-benzyl-piperazine-1-carboxylic acid methylamide is subjected to hydrogenation over palladium on carbon catalyst in a methanol/hydrochloric acid mixture to give the title compound as a hydrochloride salt.

Preparation A-2

1-(2-Hydroxyacetyl)-piperazine

It is envisaged that the title compound will be preparable by the following sequence of reactions:

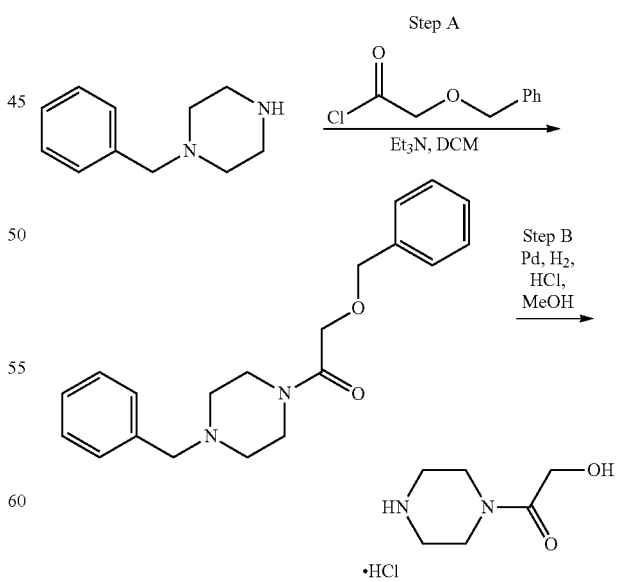

1-Benzylpiperazine is reacted with 2-benzyloxyacetyl chloride in dichloromethane in the presence of triethylamine to give 2-benzyloxy-1-(4-benzyl-piperazin-1-yl)-ethanone which is then hydrogenated over a palladium on carbon catalyst in a methanol/hydrochloric acid mixture to remove the benzyl group and give the title compound.

Preparation A-3

4-Methanesulphonylpiperidine

4-Methylsulphonylpiperidine can be prepared by the sequence of steps set out in the Scheme below and by using the conditions and reagents described in WO00/50391, page 45, example 65.

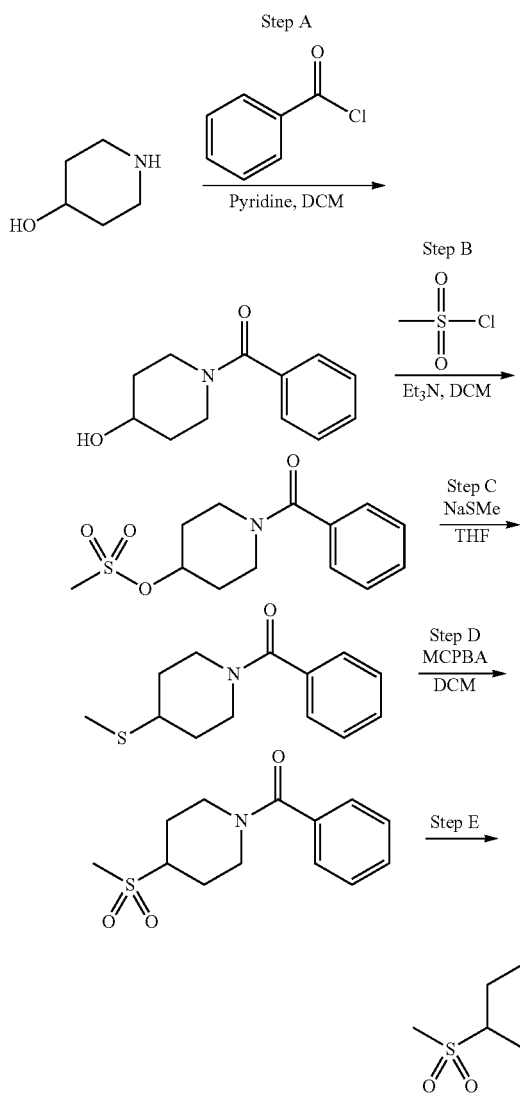

Preparation of 2-Chloropyridine Intermediates

General Method I

2-Chloropyridine intermediates can be prepared from 2-choro-4-formylpyridine by reductive amination with an amine $R^2R^3NH$ in the presence of sodium triacetoxyborohydride and acetic acid under the conditions described in Tetrahedron (2006), 62(6), 1110-1115.

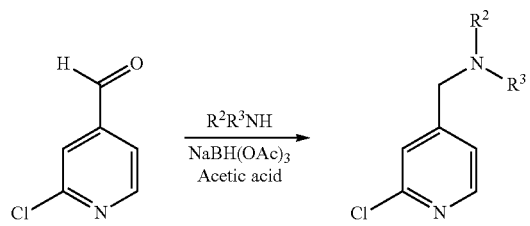

By following General Method I, the following 2-chloropyridine compounds can be prepared:

| Preparation | 2-Chloropyridine Compound | Starting Amine $R^2R^3NH$ |
|---|---|---|
| B-1 | | 1-Acetylpiperazine, Sigma-Aldrich, 359513 |
| B-2 | | 1-Methanesulphonyl-piperazine, Fluorochem, 022119 |
| B-3 | | Piperazine, Sigma-Aldrich, W425001 |
| B-4 | | Morpholine, Sigma-Aldrich |

| Preparation | 2-Chloropyridine Compound | Starting Amine R²R³NH |
|---|---|---|
| B-5 | [4-((2-chloropyridin-4-yl)methyl)piperazine-1-carboxamide structure] | Piperazine-1-carboxylic acid amide HCl, Fluorochem, 019609 |
| B-6 | [4-((2-chloropyridin-4-yl)methyl)-N,N-dimethylpiperazine-1-carboxamide structure] | Piperazine-1-carboxylic acid dimethylamide, Fluorochem, 021299 |
| B-7 | [4-((2-chloropyridin-4-yl)methyl)-N-methylpiperazine-1-carboxamide structure] | Piperazine-1-carboxylic acid methylamide Preparation A-1 |
| B-8 | [1-(4-((2-chloropyridin-4-yl)methyl)piperazin-1-yl)-2-hydroxyethanone structure] | 1-(2-Hydroxyacetyl)-piperazine Preparation A-2 |
| B-9 | [1-((2-chloropyridin-4-yl)methyl)-4-(methylsulfonyl)piperidine structure] | 4-Methanesulphonyl-piperidine Preparation A-3 |
| B-10 | [4-((2-chloropyridin-4-yl)methyl)thiomorpholine 1,1-dioxide structure] | Thiomorpholine 1,1-dioxide, 3B Scientific Corporation, 3B3-019531 |

Preparation B-11

A. 2-Chloro-4-(chloromethyl)pyridine

Boron trifluoride diethyl etherate (71 g, 0.5 mol) was added dropwise to a suspension of 2-chloroisonicotinic acid (20 g, 0.125 mol) and sodium borohydride (14.3 g, 0.376 mol) in THF (200 mL) with stirring at −10~−5° C., then the mixture was stirred at room temperature overnight. The reaction mixture was quenched with water (100 mL), and extracted with ethyl acetate (3×200 mL). The organic layers were combined, washed with brine (200 mL), dried over anhydrous $Na_2SO_4$, filtered and concentrated to dryness. The crude material was further purified by silica gel chromatography (EtOAc/Hexane=1/4) and afforded 2-chloro-4-(hydroxymethyl)pyridine (15.4 g, 85.8% yield) as an oil.

$SOCl_2$ (4.2 g, 35.5 mol) was added dropwise to a suspension of the alcohol (5 g, 34.8 mmol) in $CH_2Cl_2$ (50 mL) at −5° C. with stirring. The mixture was stirred at room temperature overnight, then quenched with water (100 mL), and extracted with $CH_2Cl_2$ (3×100 mL). The organic layers were combined, washed with brine (200 mL), dried over anhydrous $Na_2SO_4$, filtered and concentrated to dryness. The crude material was further purified by silica gel chromatography (EtOAc/Hexane=1/5) and afforded the title compound (5.5 g, near quantitative yield) as an oil.

B. 2-Chloro-4-(pyrrolidin-1-ylmethyl)pyridine

A solution of 2-chloro-4-(chloromethyl)pyridine (1.6 g, 12.3 mmol) in acetonitrile (10 mL) was added dropwise to a solution of pyrrolidine (4 g, 61.7 mmol) in acetonitrile (30 mL) at 0° C., then the mixture was stirred at room temperature overnight. The reaction mixture was quenched with water (100 mL), and extracted with ethyl acetate (3×100 mL). The organic layers were combined, washed with brine (100 mL), dried over anhydrous $Na_2SO_4$, filtered and concentrated to dryness. The crude material was further purified by silica gel chromatography (EtOAc/Hexane=1/6) and afforded 5 (1.5 g, 62% yield) as an oil. $^1$H NMR (300 MHz, $CDCl_3$): 8.31 (d, J=4.8 Hz, 1H), 7.34 (s, 1H), 7.21 (d, J=4.8 Hz, 1H), 3.61 (s, 2H), 2.51 (m, 4H), 1.81 (m, 4H).

Preparation B-12

1-(2-Chloro-pyridin-4-ylmethyl)-4-(N-methylcarbamoyl)piperazine

A. 1-Boc-4-(chlorocarbonyl)piperazine

A solution of N-Boc-piperazine (10, 20 g, 0.11 mol) and pyridine (12.9 g, 1.5 equiv) in dichloromethane (200 ml) was added dropwise to a solution of triphosgene (40.3 g, 1.2 equiv) in dichloromethane at 0-5° C. The cooling bath was removed and the mixture warmed to room temperature over 30 min. The mixture was quenched by the dropwise addition of 1M HCl. The organic layer was separated and washed successively with 1M HCl, water and saturated NaCl solution, dried over anhydrous Na$_2$SO$_4$ and evaporated in vacuo to give compound 5 (16 g, yield 60%) as a yellow solid.

B. 1-Boc-4-(N-methylcarbamoyl)piperazine

A solution of 1-Boc-4-(chlorocarbonyl)piperazine (300 mg, 1.22 mmol), pyridine (288.4 mg, 3 equiv), and methylamine (1.83 mmol, 1.5 equiv) in dichloromethane was refluxed overnight. The solution was quenched by the dropwise addition of water. The organic layer was separated, dried over anhydrous Na$_2$SO$_4$, and evaporated in vacuo. The residue was purified by flash chromatography to give the title compound as a solid (~70% yield).

C. 1-(2-Chloro-pyridin-4-ylmethyl)-4-(N-methylcarbamoyl)piperazine

1-Boc-4-(N-methylcarbamoyl)piperazine was treated with 8 M HCl/EtOAc to afford a salt, then the salt (1.0 equiv) was mixed with 2-chloro-4-(chloromethyl)pyridine (1.0 equiv) (Preparation B-11) and K$_2$CO$_3$ (4 equiv) in DMF. The mixture was stirred for 1 h at rt. After removing most of the solvent, the residue was partitioned in water and EtOAc. The organic layer was separated, dried over anhydrous Na$_2$SO$_4$, and evaporated in vacuo. The residue was purified by flash chromatography to give the title compound as a solid (~90% yield).

Preparation B-13

1-(2-Chloro-pyridin-4-ylmethyl)-4-(N,N-dimethylcarbamoyl)piperazine

A. 1-Boc-4-(N,N-dimethylcarbamoyl)piperazine

A solution of 1-Boc-4-(chlorocarbonyl)piperazine (300 mg, 1.22 mmol), pyridine (288.4 mg, 3 equiv) (Preparation B-12-A), and dimethylamine (1.83 mmol, 1.5 equiv) in dichloromethane was refluxed overnight. The solution was quenched by the dropwise addition of water. The organic layer was separated, dried over anhydrous Na$_2$SO$_4$, and evaporated in vacuo. The residue was purified by flash chromatography to give the title compound as a solid (~70% yield).

B. 1-(2-Chloro-pyridin-4-ylmethyl)-4-(N,N-dimethylcarbamoyl)piperazine

1-Boc-4-(N,N-dimethylcarbamoyl)piperazine was treated with 8 M HCl/EtOAc to afford a salt, then the salt (1.0 equiv) was mixed with 2-chloro-4-(chloromethyl)pyridine (1.0 equiv) (Preparation B-11) and K$_2$CO$_3$ (4 equiv) in DMF. The mixture was stirred for 1 h at rt. After removing most of the solvent, the residue was partitioned in water and EtOAc. The organic layer was separated, dried over anhydrous Na$_2$SO$_4$, and evaporated in vacuo. The residue was purified by flash chromatography to give the title compound as a solid (~90% yield).

Preparation B-14

1-Boc-4-(2-chloropyridin-4-ylmethyl)piperazine

To a mixture of 2-chloro-4-(chloromethyl)pyridine (500 mg, 2.05 mmol) and K$_2$CO$_3$ (1.14 g, 4 equiv) in DMF (50 ml), was added N-Boc-piperazine (558 mg, 1.1 equiv.). The mixture was stirred at rt for 1 h, after which TLC showed that no starting materials remained. The DMF was removed under vacuum and the residue was partitioned between water and ethyl acetate. The organic layer was collected, dried over anhydrous Na$_2$SO$_4$, concentrated, and applied onto a silica gel column. The title compound (570 mg, yield 91%) was obtained as a colorless gel.

Preparation B-15

1-Acetyl-4-(2-chloropyridin-4-ylmethyl)piperazine

A. 1-Acetyl-4-tert-butoxycarbonylpiperazine

A solution of N-Boc-piperazine (300 mg, 1.63 mmol), triethylamine (494 mg, 3 equiv), and acetyl chloride (1.5 equiv) in dichloromethane was stirred overnight at rt. The solution was quenched by the dropwise addition of water. The organic layer was separated, dried over anhydrous Na$_2$SO$_4$, and evaporated in vacuo. The residue was purified by flash chromatography to give the title compound (~85% yield) as a solid.

B. N-Acetylpiperazine

1-Acetyl-4-tert-butoxycarbonylpiperazine was treated with 8 M HCl/EtOAc to afford the title compound in near quantitative yield.

C. 1-(2-Chloropyridin-4-ylmethyl)-4-acetylpiperazine

N-Acetylpiperazine (1.0 equiv) was mixed with compound 2-chloro-4-(chloro-methyl)pyridine (1.0 equiv) and K$_2$CO$_3$ (4 equiv) in DMF. The mixture was stirred for 1 h at rt. After removing most of the solvent, the residue was partitioned in water and EtOAc. The organic layer was separated, dried over anhydrous Na$_2$SO$_4$, and evaporated in vacuo. The residue was purified by flash chromatography to give the title compound as a solid.

Preparation B-16

1-Benzyloxyacetyl-4-(2-chloropyridin-4-ylmethyl)piperazine

A. 1-Benzyloxyacetyl-4-tert-butoxycarbonylpiperazine

A solution of N-Boc-piperazine (300 mg, 1.63 mmol), triethylamine (494 mg, 3 equiv), and benzyloxyacetyl chloride (1.5 equiv) in dichloromethane was stirred overnight at rt. The solution was quenched by the dropwise addition of water. The organic layer was separated, dried over anhydrous Na$_2$SO$_4$, and evaporated in vacuo. The residue was purified by flash chromatography to give the title compound (~85% yield) as a solid.

B. N-Benzyloxyacetyl-piperazine

1-Benzyloxyacetyl-4-tert-butoxycarbonylpiperazine was treated with 8 M HCl/EtOAc to afford the title compound in near quantitative yield.

C. 1-(2-Chloropyridin-4-ylmethyl)-4-benzyloxyacetylpiperazine

N-Benzyloxyacetyl-piperazine (1.0 equiv) was mixed with the compound 2-chloro-4-(chloro-methyl)pyridine (1.0 equiv) and $K_2CO_3$ (4 equiv) in DMF. The mixture was stirred for 1 h at rt. After removing most of the solvent, the residue was partitioned in water and EtOAc. The organic layer was separated, dried over anhydrous $Na_2SO_4$, and evaporated in vacuo. The residue was purified by flash chromatography to give the title compound as a solid.

Preparation of Isoquinoline Amine Intermediates

Preparation C-1

6-chloroisoquinolin-3-amine

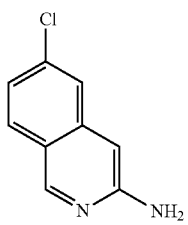 [SMILES: Nc1cc2cc(Cl)ccc2cn1]

The title compound can be made by the method described in Example 1 of WO2007/125405 but using 1-(4-chlorophenyl)methanamine rather than 1-(4-bromophenyl)methanamine

Preparation C-2

6-(1H-Pyrazol-4-yl)isoquinolin-3-amine

The title compound can be made by the method described in Example 1 of WO2007/125405 but using 6-chloroisoquinolin-3-amine rather than 6-bromoisoquinoline and using bis(tri-tert-butylphosphine)palladium(0) as catalyst.

Preparation C-3

5-Fluoro-8-methyl-isoquinolin-3-ylamine

The title compound can be made by the method described in WO2007/125405, as follows:

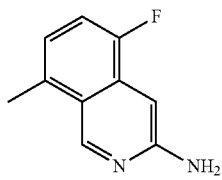

The title compound can be prepared by the method of Preparation C-1 but using 1-(5-fluoro-2-methylphenyl)methanamine instead of 1-(4-bromophenyl)methanamine.

Preparation C-4

7-Fluoro-5-trifluoromethyl-isoquinolin-3-ylamine

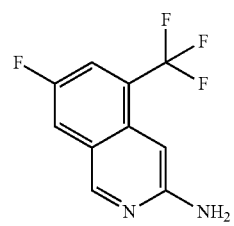 [SMILES: Nc1cc2c(C(F)(F)F)cc(F)cc2cn1]

The title compound can be prepared by following the procedures described in WO2007/125405 and using the method of Preparation C-1 above but using 1-(3-fluoro-5-trifluoromethylphenyl)methanamine instead of 1-(4-bromophenyl)methanamine.

Preparation C-5

6-Chloro-8-methylisoquinolin-3-amine

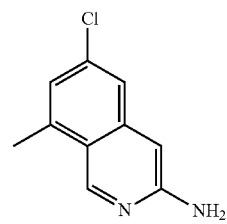

It is envisaged that the title compound can be prepared by following the procedures described in WO2007/125405 and using the method of Preparation C-1 above but using 1-(4-chloro-2-methylphenyl)methanamine instead of 1-(4-bromophenyl)methanamine.

Preparation C-6

6,7-Difluoroisoquinolin-3-amine

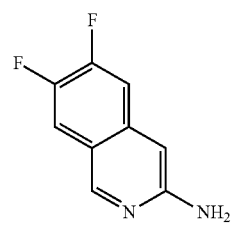

It is envisaged that the title compound can be prepared as described in WO2007/125405 by the method of Preparation C-1 but using 1-(3,4-difluorophenyl)methanamine instead of 1-(4-bromophenyl)methanamine.

Preparation C-7

6,7-Dimethoxyisoquinolin-3-amine

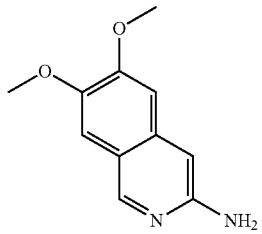

It is envisaged that the title compound can be prepared as described in WO2007/125405 by the method of Preparation C-1 but using 1-(3,4-dimethoxyphenyl)methanamine instead of 1-(4-bromophenyl)methanamine.

Preparation C-8

6-Methoxy-isoquinolin-3-ylamine

The title compound can be made by the method described in Example 3a on page 96 of WO2007/125405, as follows:

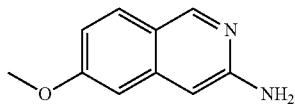

Preparation C-9

7-Chloro-isoquinolin-3-ylamine

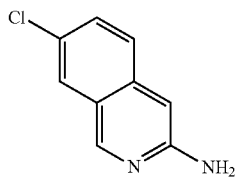 [SMILES: Nc1cc2ccc(Cl)cc2cn1]

A. 3-(4-Chlorophenyl)-2-formylamino-propanoic acid methyl ester

SOCl$_2$ (18 g, 0.15 mol) was added dropwise to a suspension of 4-(chlorophenyl)alanine (20 g, 0.1 mol) in MeOH (200 mL) at −5° C. with stirring. The mixture was stirred for 2 hours at room temperature, then heated under reflux for 4 hours. After cooling to room temperature, the solvent was distilled off under reduced pressure. The residue was suspended in CH$_2$Cl$_2$ (200 mL), and EDC (20 g, 105 mmol), N-methylmorpholine (10.5 g, 105 mmol) and formic acid (4.5 mL) were added. The mixture was stirred for 15 minutes, formic acid (4.5 mL) was added, and the mixture was stirred for a further 15 minutes. This addition step was repeated three times and the reaction mixture was diluted with CH$_2$Cl$_2$ (200 mL) and water (500 mL). The organic layer was separated, and the aqueous layer was re-extracted with CH$_2$Cl$_2$ (2×200 mL). The organic layers were combined, washed with brine (200 mL), dried over anhydrous Na$_2$SO$_4$, filtered and concentrated to dryness. The crude material was further purified by silica gel chromatography (EtOAc/Hexane=1/10) and afforded the title compound (15 g, 62.2% yield) as an oil.

B. 7-Chloroisoquinoline-3-carboxylic acid

Oxalyl choride (5.7 mL) was added dropwise to a solution of 3-(4-chlorophenyl)-2-formylamino-propanoic acid methyl ester (14.5 g, 60 mmol) in CH$_2$Cl$_2$ (400 mL) at room temperature. After stirring for 0.5 hour, ferric chloride (11.7 g) was added and the mixture was stirred for 48 hours. The reaction mixture was diluted with water (500 mL). The organic layer was separated, and the aqueous layer was re-extracted with CH$_2$Cl$_2$ (2×300 mL). The organic layers were combined, washed with brine (200 mL), dried over anhydrous Na$_2$SO$_4$, filtered and concentrated to dryness. The residue was dissolved in MeOH (400 mL), sulfuric acid (20 mL, 98%) was added and the mixture was heated under reflux for 48 hours. After cooled to room temperature, the reaction mixture was diluted with 5% sodium bicarbonate solution (1 L). The organic layer was separated, and the aqueous layer was re-extracted with CH$_2$Cl$_2$ (2×500 mL). The organic layers were combined, washed with brine (500 mL), dried over anhydrous Na$_2$SO$_4$, filtered and concentrated to dryness. The crude material was further purified by silica gel chromatography (EtOAc/Hexane=1/3) and afforded the title compound (3.1 g, 23.3% yield) as a yellow solid. $^1$H NMR (300 MHz, CDCl$_3$): 9.26 (s, 1H), 8.51 (s, 1H), 8.05 (d, J=1.8 Hz, 1H), 7.93 (d, J=8.7 Hz, 1H), 7.73 (dd, J=1.8 and 8.7 Hz, 1H), 4.06 (s, 3H).

C. 7-Chloroisoquinolin-3-amine

7-Chloroisoquinoline-3-carboxylic acid (3.1 g, 14 mmol) was dissolved in 6 N HCl (50 mL), and the mixture was heated under reflux for 4 hours. After cooling to room temperature, the solvent was distilled off under reduced pressure. The residue was dissolved in tert-butanol (100 mL), and triethylamine (2.8 g, 28 mmol) and diphenylphosphoryl azide (5.6 mL, 26 mmol) were added. The mixture was heated under reflux overnight. After cooled to room temperature, the solvent was distilled off under reduced pressure. The crude material was further purified by silica gel chromatography (EtOAc/Hexane=1/1) and afforded the title compound (500 mg, 20% yield) as a yellow solid. $^1$H NMR (300 MHz, DMSO-d6): 8.62 (s, 1H), 7.66 (d, J=9 Hz, 1H), 6.86 (d, J=2.4, 1H), 6.75 (dd, J=2.4 and 9 Hz, 1H), 6.52 (s, 1H), 5.83 (s, 1H), 3.83 (s, 3H); MS: m/z 174.1 (M+H⁺).

Preparation C-10

6-Methoxyisoquinolin-3-amine

A. 2,2-Diethoxy-N-(4-methoxybenzyl)acetimidamide

A solution of sodium methoxide (23%, 4.1 mL, 16 mmol) in MeOH was added to a solution of diethoxyacetonitrile (22 g, 86 mmol) in MeOH (400 mL) with stirring. The solution was stirred at room temperature overnight. The solvent was distilled off under reduced pressure. The residue was dissolved in diethyl ethyl (200 mL) and washed with washed with brine (200 mL), dried over anhydrous Na₂SO₄, filtered and concentrated to dryness. The crude material was dissolved in MeOH (100 mL), and p-methoxybenzylamine (11 g, 80 mmol) was added. Then this solution was heated under reflux overnight. After cooled to room temperature, the solvent was distilled off under reduced pressur to give the crude title compound (23 g).

B. 6-Methoxyisoquinolin-3-amine

The crude 2,2-diethoxy-N-(4-methoxybenzyl)acetimidamide (23 g) was added dropwise to conc. sulfuric acid (200 mL) at 20~25° C. with stirring. The mixture was stirred at room temperature for 48 hours and then quenched with ice (1 Kg). 12 N NaOH solution (400 mL) was added to give a final pH of 9~10. The resulting suspension was extracted with CH₂Cl₂ (5×2 L). The organic layers were combined, washed with brine (500 mL), dried over anhydrous Na₂SO₄, filtered and concentrated to dryness. The crude material was further purified by silica gel chromatography (EtOAc/Hexane=1/1) and afforded the title compound (430 mg, 2.9% yield based on p-methoxybenzylamine) as a yellow solid. ¹H NMR (300 MHz, DMSO-d6): 8.62 (s, 1H), 7.66 (d, J=9 Hz, 1H), 6.86 (d, J=2.4, 1H), 6.75 (dd, J=2.4 and 9 Hz, 1H), 6.52 (s, 1H), 5.83 (s, 1H), 3.83 (s, 3H); MS: m/z 175.1 (M+H⁺).

Preparation C-11

7-Fluoroisoquinolin-3-amine

A. 2,2-Diethoxy-N-(3-fluorobenzyl)acetimidamide

A solution of sodium methoxide (23%, 4.1 mL, 16 mmol) in MeOH was added to a solution of diethoxyacetonitrile (22 g, 86 mmol) in MeOH (400 mL) with stirring. The solution was stirred at room temperature overnight. The solvent was distilled off under reduced pressure. The residue was dissolved in diethyl ethyl (200 mL) and washed with washed with brine (200 mL), dried over anhydrous Na₂SO₄, filtered and concentrated to dryness. The crude material was dissolved in MeOH (100 mL), and m-fluorobenzylamine (10 g, 80 mmol) was added. Then this solution was heated under reflux overnight. After cooled to room temperature, the solvent was distilled off under reduced pressure to give the crude title compound (22 g).

B. 7-Fluoroisoquinolin-3-amine

The crude 2,2-diethoxy-N-(3-fluorobenzyl)acetimidamide (22 g) was added dropwise to conc. sulfuric acid (200 mL) at 20~25° C. with stirring. The mixture was stirred at room temperature for 48 hours. Then this mixture was quenched with ice (1 Kg), and a 12 N NaOH solution (400 mL) was added. The final pH of 9~10 was reached. The suspension was extracted with CH₂Cl₂ (5×2 L). The organic layers were combined, washed with brine (500 mL), dried over anhydrous Na₂SO₄, filtered and concentrated to dryness. The crude material was purified by silica gel chromatography (EtOAc/Hexane=1/1) and afforded the title compound (330 mg, 2.5% yield based on m-fluorobenzylamine) as a yellow solid. ¹H NMR (300 MHz, CDCl₃): 9.17 (s, 1H), 8.66 (s, 1H), 8.01~8.07 (m, 2H), 7.68 (dd, J=2.4, and 8.7 Hz, 1H), 7.58 (m, 1H); MS: m/z 163.1 (M+H⁺).

EXAMPLES

Example 1

Isoquinolin-3-yl-(4-pyrrolidin-1-ylmethyl-pyridin-2-yl)-amine

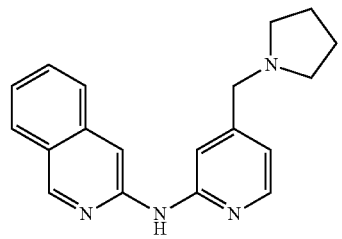 [SMILES: c1ccc2cc(Nc3cc(CN4CCCC4)ccn3)ncc2c1]

2-Chloro-4-pyrrolidin-1-ylmethyl-pyridine (1 eq), isoquinoline-3-ylamine (1 eq), 2.0 eq. of caesium carbonate, 10% (mol) Xantphos and 10% (mol) of Pd₂(dba)₃ were mixed in toluene (3 ml). The reaction mixture was degassed for three times and then warmed to 100° C. overnight. The reaction mixture was cooled, concentrated and purified by column chromatography eluting 0-10% sat. NH₃/MeOH and DCM to afford the title compound.

LCMS r.t. 2.93 305.3 (MH⁺, ES⁺)
¹H NMR (DMSO-d6): δ 11.17-10.94 (1H, br s), 9.22 (1H, s), 8.40 (1H, d), 8.18-8.08 (2H, br m), 7.93 (1H, br d), 7.75 (1H, br t), 7.57-7.49 (2H, m), 7.35-7.29 (1H, br m), 4.45 (2H, br d), 3.47-3.42 (2H, m), 3.15-3.03 (2H, m), 2.11-1.98 (2H, m), 1.97-1.85 (2H, m).

Examples 2 to 13

By following the method described in Example 1 and using the appropriate isoquinoline amine and chloropyridine, the compounds of Examples 2 to 13 can be prepared.

| Example | Compound | Isoquinoline starting material | Chloropyridine starting material |
|---|---|---|---|
| 2 | 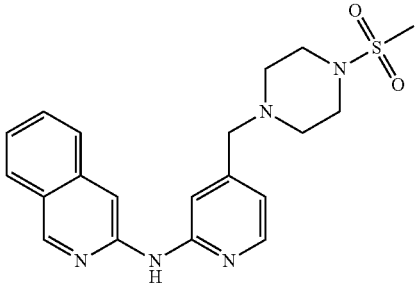 [SMILES: CS(=O)(=O)N1CCN(Cc2ccnc(Nc3cc4ccccc4cn3)c2)CC1] | isoquinoline-3-ylamine | Preparation B-2 |
| 3 | 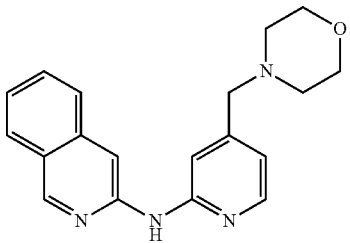 [SMILES: c1ccc2cc(Nc3cc(CN4CCOCC4)ccn3)ncc2c1] | isoquinoline-3-ylamine | Preparation B-4 |
| 4 | 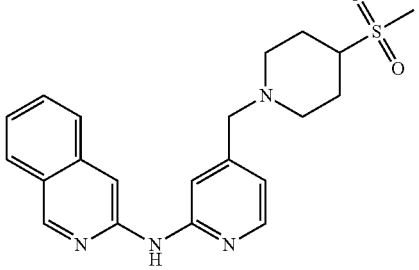 | isoquinoline-3-ylamine | Preparation B-9 |
| 5 | 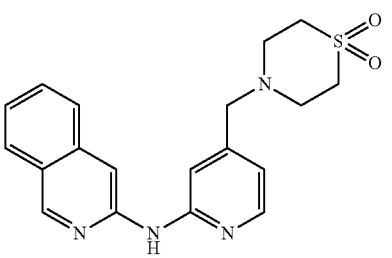 [SMILES: O=S1(=O)CCN(Cc2ccnc(Nc3cc4ccccc4cn3)c2)CC1] | isoquinoline-3-ylamine | Preparation B-10 |
| 6 | 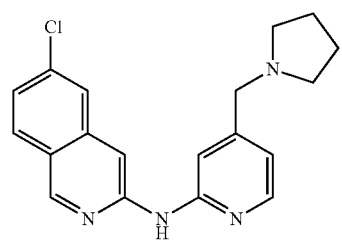 [SMILES: Clc1ccc2cnc(Nc3cc(CN4CCCC4)ccn3)cc2c1] | Preparation C-1 | 2-Chloro-4-pyrrolidin-1-ylmethyl-pyridine |

-continued

| Example | Compound | Isoquinoline starting material | Chloropyridine starting material |
|---------|----------|-------------------------------|----------------------------------|
| 7 | 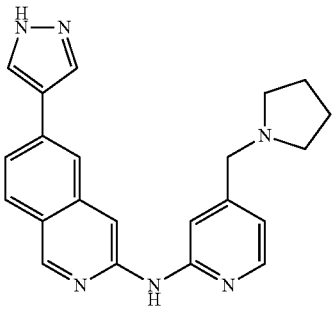 [SMILES: c1cc(CN2CCCC2)cc(Nc2cc3cc(-c4cn[nH]c4)ccc3cn2)n1] | Preparation C-2 | 2-Chloro-4-pyrrolidin-1-ylmethyl-pyridine |
| 8 | 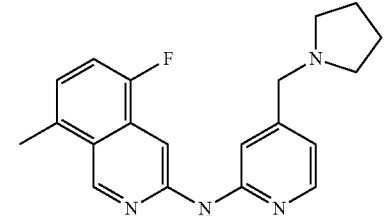 | Preparation C-3 | 2-Chloro-4-pyrrolidin-1-ylmethyl-pyridine |
| 9 | 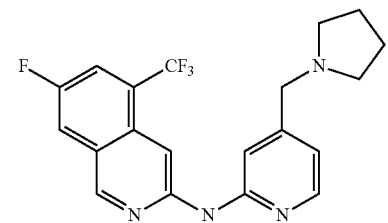 | Preparation C-4 | 2-Chloro-4-pyrrolidin-1-ylmethyl-pyridine |
| 10 | 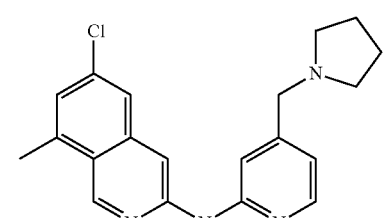 | Preparation C-5 | 2-Chloro-4-pyrrolidin-1-ylmethyl-pyridine |
| 11 | 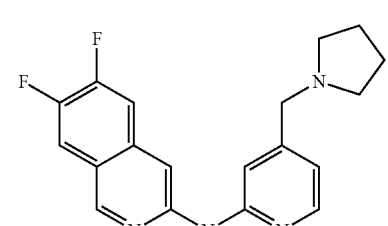 | Preparation C-6 | 2-Chloro-4-pyrrolidin-1-ylmethyl-pyridine |
| 12 | 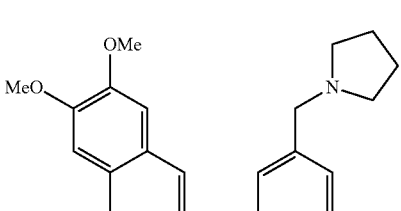 | Preparation C-7 | 2-Chloro-4-pyrrolidin-1-ylmethyl-pyridine |

| Example | Compound | Isoquinoline starting material | Chloropyridine starting material |
|---------|----------|-------------------------------|----------------------------------|
| 13 | 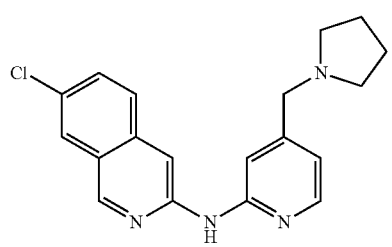 [SMILES: Clc1ccc2cc(Nc3cc(CN4CCCC4)ccn3)ncc2c1] | Preparation C-8 | 2-Chloro-4-pyrrolidin-1-ylmethyl-pyridine |

Example 14

7-Chloroisoquinolin-3-yl-(4-pyrrolidin-1-ylmethyl-pyridin-2-yl)-amine

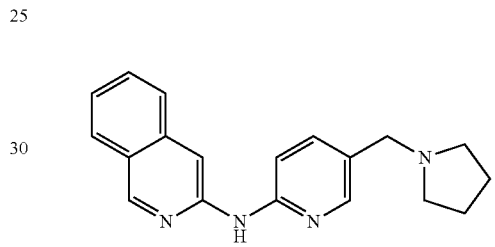

Pd$_2$(dba)$_3$(102 mmg, 0.11 mmol) and xantphos (92 mg, 0.16 mmol) were added to a solution of 7-chloroisoquinolin-3-amine (200 mg, 1.12 mmol) (Preparation C-9), 2-chloro-4-pyrrolidin-1-ylmethyl-pyridine (220 mmg, 1.12 mmol) (Preparation B-11) and Cs$_2$CO$_3$ (500 mg, 1.53 mmol) in toluene (50 mL). The suspension was heated under reflux overnight, and THF (50 mL) was added in to dilute the mixture. After filtration, the filtrate was concentrated. The crude material was further purified by silica gel chromatography (EtOAc/Hexane=1/1) and afforded the title compound (120 mg, 32% yield) as a yellow solid.

$^1$H NMR (300 MHz, DMSO-d6): 8.89 (s, 1H), 8.43 (s, 1H), 8.28 (d, J=5.4 Hz, 1H), 7.82 (s, 1H), 7.72 (d, J=9, 1H), 7.40~7.55 (m, 2H), 7.02 (s, 1H), 6.88 (d, J=1.5 Hz, 1H), 3.63 (s, 2H), 2.58 (m, 4H), 1.86 (m, 4H); MS: m/z 339.0 (M+H$^+$).

Example 15

Isoquinolin-3-yl-(5-pyrrolidin-1-ylmethyl-pyridin-2-yl)-amine

Step A

2-Chloro-5-pyrrolidin-1-ylmethyl-pyridine

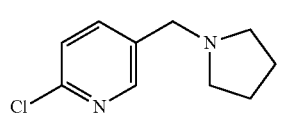

The title compound can be prepared using the reductive amination procedure described in General Method I but substituting 6-chloropyridine-3-carboxaldehyde (Sigma-Aldrich, Compound number: 596175) for 2-chloro-4-formylpyridine.

Step B

Isoquinolin-3-yl-(5-pyrrolidin-1-ylmethyl-pyridin-2-yl)-amine

The title compound can be prepared by reacting 2-chloro-5-pyrrolidin-1-ylmethyl-pyridine with isoquinoline-3-ylamine under the conditions described in Example 1.

Example 16

Isoquinolin-3-yl-[4-(3-pyrrolidin-1-yl-propoxy)-pyridin-2-yl]-amine

Step A

2-Chloro-4-(3-pyrrolidin-1-yl-propoxy)-pyridine

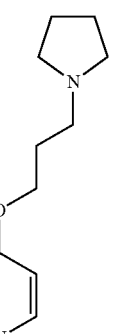

It is envisaged that the title compound can be prepared by reacting 6-chloro-4-hydroxypyridine (Aldrich) with sodium hydride and then 3-pyrrolidin-1-yl-propyl bromide (APAC Pharmaceutical Product List; Beta Pharma, Inc., New Haven, Conn., USA) using the conditions described in Example 1 on page 7 of EP0269457.

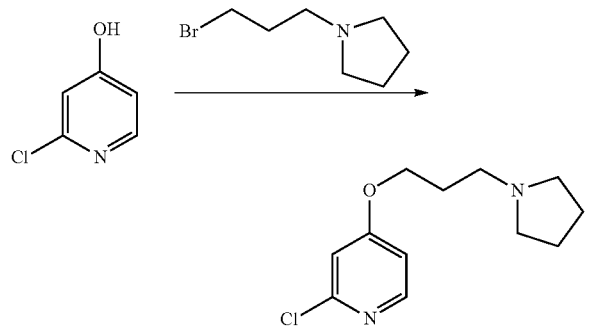

Step B

Isoquinolin-3-yl-[4-(3-pyrrolidin-1-yl-propoxy)-pyridin-2-yl]-amine

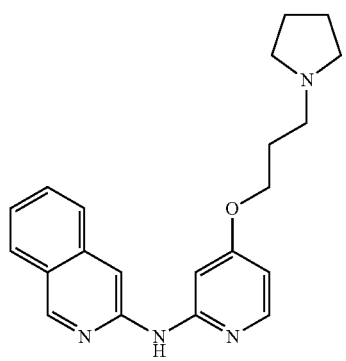 [SMILES: c1ccc2cc(Nc3cc(OCCCN4CCCC4)ccn3)ncc2c1]

The title compound can be prepared by reacting isoquinoline-3-ylamine with 2-chloro-4-(3-pyrrolidin-1-yl-propoxy)-pyridine under the conditions described in Example 1.

Example 17

(6-Methoxy-isoquinolin-3-yl)-(4-pyrrolidin-1-ylmethyl-pyridin-2-yl)-amine

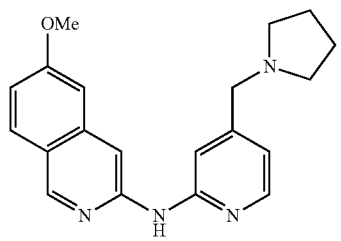 [SMILES: COc1ccc2cnc(Nc3cc(CN4CCCC4)ccn3)cc2c1]

Pd$_2$(dba)$_3$(102 mmg, 0.11 mmol) and xantphos (92 mg, 0.16 mmol) were added to a solution of 6-methoxyisoquinolin-3-amine (195 mg, 1.12 mmol) (Preparation C-10), 2-chloro-4-pyrrolidin-1-ylmethyl-pyridine (220 mg, 1.12 mmol) (Preparation B-11) and Cs$_2$CO$_3$ (500 mg, 1.53 mmol) in toluene (50 mL). The suspension was heated under reflux overnight, and THF (50 mL) was added in to dilute the mixture. After filtration, the filtrate was concentrated. The crude material was further purified by silica gel chromatography (EtOAc/Hexane=1/1) and afforded the title compound (150 mg, 40% yield) as a yellow solid. $^1$H NMR (300 MHz, DMSO-d6): 8.84 (s, 1H), 8.27~8.29 (m, 2H), 7.73 (d, J=8.7 Hz, 1 H), 7.60 (bs, 1H), 6.99~7.08 (m, 3H), 7.02 (s, 1H), 6.86 (d, J=5.1 Hz, 1H), 3.94 (s, 3H), 3.62 (s, 2H), 2.58 (m, 4H), 1.83 (m, 4H); MS: m/z 335.2 (M+H$^+$).

Example 18

7-Fluoroisoquinolin-3-yl-(4-pyrrolidin-1-ylmethyl-pyridin-2-yl)-amine

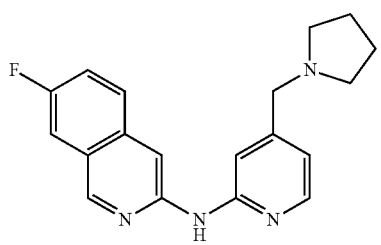 [SMILES: Fc1ccc2cc(Nc3cc(CN4CCCC4)ccn3)ncc2c1]

Pd$_2$(dba)$_3$(102 mmg, 0.11 mmol) and xantphos (92 mg, 0.16 mmol) were added to a solution of 7-fluoroisoquinolin-3-amine (182 mg, 1.12 mmol) (Preparation C-11), 2-chloro-4-pyrrolidin-1-ylmethyl-pyridine (220 mg, 1.12 mmol) (Preparation B-11) and Cs$_2$CO$_3$ (500 mg, 1.53 mmol) in toluene (50 mL). The suspension was heated under reflux overnight, and THF (50 mL) was added in to dilute the mixture. After filtration, the filtrate was concentrated. The crude material was further purified by silica gel chromatography (EtOAc/Hexane=1/1) and afforded the title compound (115 mg, 31.8% yield) as a yellow solid. $^1$H NMR (300 MHz, DMSO-d6): 8.94 (s, 1H), 8.42 (s, 1H), 8.27 (d, J=5.4 Hz, 1H), 7.72~7.77 (m, 2H), 7.33~7.46 (m, 2H), 7.02 (s, 1H), 6.84 (d, J=5.4 Hz, 1H), 3.59 (s, 2H), 2.55 (m, 4H), 1.81 (m, 4H); MS: m/z 323.1 (M+H$^+$).

Example 19

4-[2-(Isoquinolin-3-ylamino)-pyridin-4-ylmethyl]-piperazine-1-carboxylic acid methylamide

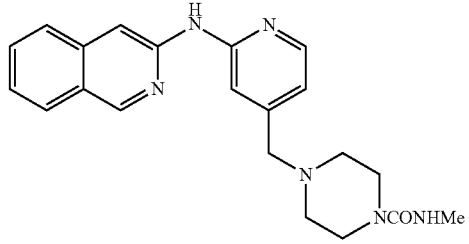

1-(2-Chloro-pyridin-4-ylmethyl)-4-(N-methylcarbamoyl) piperazine (1.0 equiv) (Preparation B-12) was mixed with 3-aminoisoquinoline (1.0 equiv), Pd$_2$(dba)$_3$ (0.1 equiv), xantphos (0.15 equiv), and Cs$_2$CO$_3$ (1.4 equiv) in toluene. The mixture was refluxed overnight, and EtOAc was added in to dilute the mixture. After filtration, the filtrate was concentrated and applied onto a silica gel column. The title compound was obtained as a yellow solid (63 mg, 28% yield): $^1$H NMR (CDCl$_3$, 300 MHz) δ: 2.49 (t, J=4.4 Hz, 4H, PyridylCH$_2$NCH$_2$CH$_2$), 2.83 (s, 6H, N(CH$_3$)$_2$), 3.29 (t, J=4.8 Hz, 4H, NCH$_2$CO), 3.52 (s, 2H, pyridylCH$_2$), 6.88-8.98 (m, 9H, isoquinolyl+pyridyl).

Example 20

4-[2-(Isoquinolin-3-ylamino)-pyridin-4-ylmethyl]-piperazine-1-carboxylic acid dimethylamide

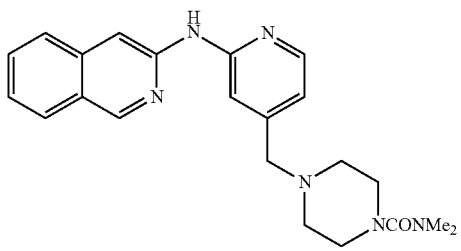

1-(2-Chloro-pyridin-4-ylmethyl)-4-(N,N-dimethylcarbamoyl)piperazine (1.0 equiv) (Preparation B-12) was mixed with 3-aminoisoquinoline (1.0 equiv), Pd$_2$(dba)$_3$ (0.1 equiv), xantphos (0.15 equiv), and Cs$_2$CO$_3$ (1.4 equiv) in toluene. The mixture was refluxed overnight, and EtOAc was added in to dilute the mixture. After filtration, the filtrate was concentrated and applied onto a silica gel column. The title compound was obtained as a yellow solid (50 mg, 22% yield): $^1$H NMR (CDCl$_3$, 300 MHz) δ: 2.47 (t, J=5.0 Hz, 4H, PyridylCH$_2$NCH$_2$CH$_2$), 2.83 (d, J=4.8 Hz, 3H, NHCH$_3$), 3.41 (t, J=5.0 Hz, 4H, NCH$_2$CO), 3.51 (s, 2H, pyridylCH$_2$), 6.86-8.99 (m, 9H, isoquinolyl+pyridyl).

Example 21

4-[2-(Isoquinolin-3-ylamino)-pyridin-4-ylmethyl]-piperazine-1-carboxylic acid amide

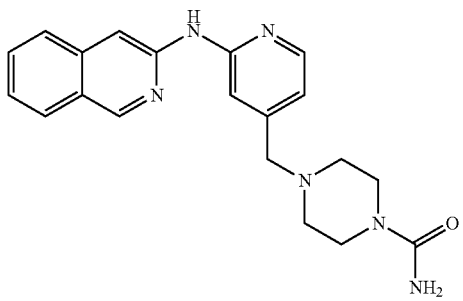 [SMILES: NC(=O)N1CCN(Cc2ccnc(Nc3cc4ccccc4cn3)c2)CC1]

A. 2-(Isoquinolin-3-ylamino)-4-(4-tert-butoxycarbonylpiperazin-1-ylmethyl)-pyridine 1-Boc-4-(2-chloropyridin-4-ylmethyl)piperazine (500 mg, 1.63 mmol) (Preparation B-14) was mixed with 3-aminoisoquinoline (234 mg, 1.0 equiv), Pd$_2$(dba)$_3$ (148 mg, 0.1 equiv), xantphos (140 mg, 0.15 equiv), and Cs$_2$CO$_3$ (735 mg, 1.4 equiv) in toluene. The mixture was refluxed overnight, and EtOAc was added in to dilute the mixture. After filtration, the filtrate was concentrated and applied onto a silica gel column. The title compound (250 mg, yield 61%) was obtained as yellow solid.

B. Isoquinolin-3-yl-(4-piperazin-1-ylmethyl-pyridin-2-yl)-amine

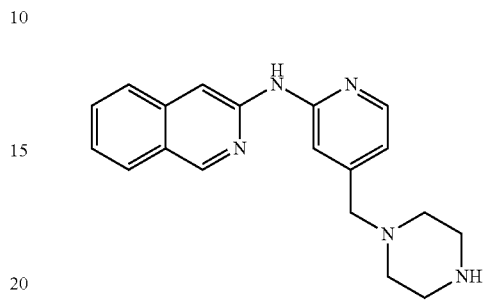

2-(Isoquinolin-3-ylamino)-4-(4-tert-butoxycarbonylpiperazin-1-ylmethyl)-pyridine was treated with 8 M HCl/EtOAc to afford the title compound as a salt in near quantitative yield (50 mg). $^1$H NMR (CDCl$_3$, 300 MHz) δ: 3.44 (s, 4H, PyridylCH$_2$NCH$_2$CH$_2$), 3.45 (s, 4H, NHCH$_2$), 4.25 (s, 2H, pyridylCH$_2$), 7.01-8.87 (m, 9H, isoquinolyl+pyridyl).

C. 2-(Isoquinolin-3-ylamino)-4-(4-carbamoylpiperazin-1-ylmethyl)pyridine

The 2-(isoquinolin-3-ylamino)-4-(piperazin-1-ylmethyl)-pyridine salt obtained from Example 21B was neutralized by NaHCO$_3$, followed by extraction with EtOAc (30 mL). The organic phase was collected, dried over anhydrous Na$_2$SO$_4$ and concentrated to afford the free amine. The amine was mixed with potassium cyanate in AcOH/Py (1/1) and the solution was stirred overnight at ambient temperature. After removal of the solvents, the resulting product was purified by flash chromatography to afford the title compound (55 mg, 60% yield). $^1$H NMR (CDCl$_3$, 300 MHz) δ: 2.49 (t, J=4.8 Hz, 4H, PyridylCH$_2$NCH$_2$CH$_2$), 3.45 (t, J=4.8 Hz, 4H, NCH$_2$CO), 3.52 (s, 2H, pyridylCH$_2$), 6.85-8.98 (m, 9H, isoquinolyl+pyridyl).

Example 22

1-[4-[2-(Isoquinolin-3-ylamino)-pyridin-4-ylmethyl]-piperazin-1-yl]-ethanone

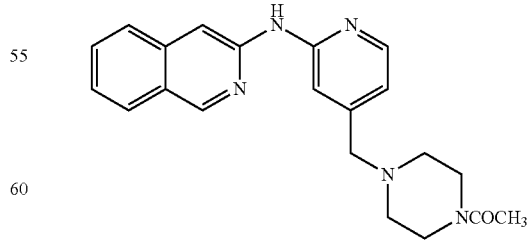

1-(2-Chloropyridin-4-ylmethyl)-4-acetylpiperazine (1.0 equiv) (Preparation B-15) was mixed with 3-aminoisoquinoline (1.0 equiv), Pd$_2$(dba)$_3$(0.1 equiv), xantphos (0.15 equiv), and Cs$_2$CO$_3$ (1.4 equiv) in toluene. The mixture was refluxed overnight, and EtOAc was added in to dilute the mixture. After filtration, the filtrate was concentrated and applied onto a silica gel column. The title compound was obtained as a yellow solid (50 mg, yield 48%). $^1$H NMR (CDCl$_3$, 300 MHz) δ: 2.10 (s, 3H, Ac), 2.47 (t, J=4.1 Hz, 4H, PyCH$_2$NCH$_2$CH$_2$), 3.58 (dt, J=4.8 Hz, 50.7 Hz, 4H, NCH$_2$CO), 3.60 (s, 2H, pyridylCH$_2$), 6.86-8.99 (m, 9H, isoquinolyl+pyridyl).

Example 23

2-Hydroxy-1-{4-[2-(isoquinolin-3-ylamino)-pyridin-4-ylmethyl]-piperazin-1-yl}-ethanone

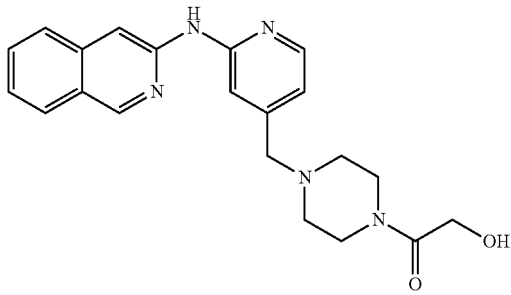 [SMILES: O=C(CO)N1CCN(Cc2ccnc(Nc3cc4ccccc4cn3)c2)CC1]

A. 2-(Isoquinolin-3-ylamino)-4-(4-benzyloxy-acetylpiperazin-1-ylmethyl)pyridine

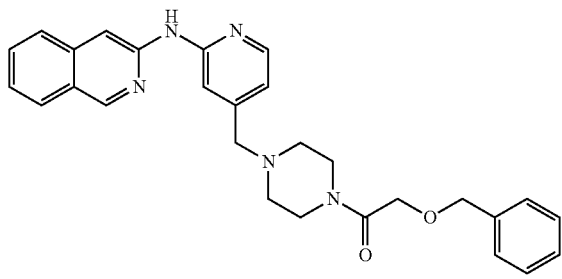 [SMILES: O=C(COCc1ccccc1)N1CCN(Cc2ccnc(Nc3cc4ccccc4cn3)c2)CC1]

1-(2-Chloropyridin-4-ylmethyl)-4-benzyloxyacetylpiperazine (1.0 equiv) (Preparation B-16) was mixed with 3-aminoisoquinoline (1.0 equiv), Pd$_2$(dba)$_3$ (0.1 equiv), xantphos (0.15 equiv), and Cs$_2$CO$_3$ (1.4 equiv) in toluene. The mixture was refluxed overnight, and EtOAc was added in to dilute the mixture. After filtration, the filtrate was concentrated and applied onto a silica gel column. The title compound was obtained as a yellow solid.

B. 2-(Isoquinolin-3-ylamino)-4-(4-(2-hydroxy-acetyl)-piperazin-1-ylmethyl)pyridine The benzyl group was removed from 2-(isoquinolin-3-ylamino)-4-(4-benzyloxyacetylpiperazin-1-ylmethyl)pyridine by treatment with HBr/AcOH to afford the title compound as a yellow solid (50 mg, yield 70%). $^1$H NMR (CDCl$_3$, 300 MHz) δ: 2.50 (t, J=8.7 Hz, 4H, PyridylCH$_2$NCH$_2$CH$_2$), 3.52 (dt, J=4.5 Hz, 123.6 Hz, 4H, NCH$_2$CO), 3.53 (s, 2H, pyridylCH$_2$), 4.17 (s, 2H, COCH$_2$OH), 6.85-8.98 (m, 9H, isoquinolyl+pyridyl).

Biological Activity

Example 24

Kinase Inhibition

Compounds of the invention can be screened for activity against a range of protein kinases using the assays set out below. Kinase inhibition assays were carried out by Millipore, Dundee Technology Park, Dundee, UK.

Aurora A

In a final reaction volume of 25 μL, Aurora-A (h) (5-10 mU) is incubated with 8 mM MOPS pH 7.0, 0.2 mM EDTA, 200 μM LRRASLG (Kemptide), 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 50 mM phosphoric acid and once in methanol prior to drying and scintillation counting.

Abl (h)

In a final reaction volume of 25 μl, Abl (h) (5-10 mU) is incubated with 8 mM MOPS pH 7.0, 0.2 mM EDTA, 50 μM EAIYAAPFAKKK, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

Arg (h)

In a final reaction volume of 25 μl, Arg (h) (5-10 mU) is incubated with 8 mM MOPS pH 7.0, 0.2 mM EDTA, 50 μM EAIYAAPFAKKK, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

Yes (h)

In a final reaction volume of 25 μl, Yes (h) (5-10 mU) is incubated with 8 mM MOPS pH 7.0, 0.2 mM EDTA, 0.1 mg/ml poly(Glu, Tyr) 4:1, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a Filtermat A and washed three times for 5 minutes in 75 mM phosphoric acid and once in methanol prior to drying and scintillation counting.

KDR (h)

In a final reaction volume of 25 μL, KDR (h) (5-10 mU) is incubated with 8 mM MOPS pH 7.0, 0.2 mM EDTA, 0.33 mg/mL myelin basic protein, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

Flt4 (h)

In a final reaction volume of 25 μL, Flt4 (h) (5-10 mU) is incubated with 8 mM MOPS pH 7.0, 0.2 mM EDTA, 500 μM GGEEEEYFELVKKKK, 10 mM MgAcetate and [□-33P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

Flt3 (h)

In a final reaction volume of 25 μL, Flt3 (h) (5-10 mU) is incubated with 8 mM MOPS pH 7.0, 0.2 mM EDTA, 50 μM EAIYAAPFAKKK, 10 mM MgAcetate and [□-33P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

c-SRC (h)

In a final reaction volume of 25 μL, c-SRC (h) (5-10 mU) is incubated with 8 mM MOPS pH 7.0, 0.2 mM EDTA, 250 μM KVEKIGEGTYGVVYK (Cdc2 peptide), 10 mM MgAcetate and [□-33P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction is then spotted onto a P30 filtermat and washed three times for 5 minutes in 75 mM phosphoric acid and once in methanol prior to drying and scintillation counting.

Results

The compound of Example 1 was tested against the KDR and Yes kinases and was found to have $IC_{50}$ values of less than 5 micromolar against each kinase.

The compounds of a number of the Examples were also tested against Flt3 and Flt4 kinases and the activities of these compounds are shown in the table below.

| Compound of Example No. | Biological activity | |
|---|---|---|
| | Mean Flt3 $IC_{50}$ (μM) | Mean Flt4 $IC_{50}$ (μM) |
| 1 | <0.1 | <0.5 |
| 14 | <0.1 | >0.1 |
| 17 | <0.1 | <0.1 |
| 18 | <0.1 | <0.1 |
| 19 | <0.1 | <0.1 |
| 20 | <0.1 | <0.1 |
| 21B | <5 | <0.5 |
| 21C | <0.1 | <0.5 |
| 22 | <0.1 | <0.5 |
| 23B | <0.1 | <0.1 |

Example 25

Anti-Proliferative Activity

The anti-proliferative activities of compounds of the invention are determined by measuring the ability of the compounds to inhibition of cell growth in a number of cell lines. Inhibition of cell growth is measured using the Alamar Blue assay The following protocol was used:
1) HT29, HCT116 or Colo205 cells were seeded at an appropriate density and allowed to adhere overnight.
2) Test compounds were prepared from 10 mM DMSO stocks to give a final concentration range as shown on the graphs. DMSO was constant throughout each experiment.
3) Test compounds were incubated with the cells for 72 h at 37° C. 5% CO2 in a humidified atmosphere.
4) Alamar blue 10% (v/v) was then added and incubated for a further 6 h, and fluorescent product detected using the BMG FLUOstar plate reader.
5) Data was analysed using a 4-parameter logistic equation in Graph Pad Prism.

The compound of Example 1 has been tested against HCT116 cells and has been found to have a cell proliferation $IC_{50}$ value of less than 25 μM.

Example 26

HT29 Colony Forming Assay

The ability of compounds of the invention to prevent growth of discrete colonies of human HT29 colon carcinoma cells over a 10 day time course can be measured using the following protocol:

1. HT29 cells (ECACC No. 91072201) are seeded in 24-well plates at a concentration of 75 cells per well and allowed to adhere overnight prior to addition of compound or vehicle control.
2. Test compounds are prepared from 10 mM DMSO stocks to give a final concentration range of 10 μM, 3 μM, 1 μM, 0.3 μM, 0.1 μM, 0.03 μM, 0.01 μM and vehicle control. The DMSO content is constant at 0.1%.
3. Test compounds are incubated with the cells for 10 days at 37° C. 5% $CO_2$ in a humidified atmosphere.
4. Colonies are fixed using Carnoy's Fixative (75% methanol, 25% acetic acid) for 5 minutes, and allowed to air dry.
5. Colonies are stained using 0.4% (w/v) crystal violet for 2 minutes.
6. Colonies (containing more than 50 cells) are counted by eye and data analysed using a 4-parameter logistic equation in GraphPad Prism.

The compound of Example 1 was found to have an $IC^{50}$ of 1.38 μM in the above assay.

Example 27

(i) Tablet Formulation

A tablet composition containing a compound of the formula (1) is prepared by mixing 50 mg of the compound with 197 mg of lactose (BP) as diluent, and 3 mg magnesium stearate as a lubricant and compressing to form a tablet in a known manner.

(ii) Capsule Formulation

A capsule formulation is prepared by mixing 100 mg of a compound of the formula (1) with 100 mg lactose and filling the resulting mixture into standard opaque hard gelatin capsules.

(iii) Injectable Formulation I

A parenteral composition for administration by injection can be prepared by dissolving a compound of the formula (1)

(e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (1) (e.g. in salt form) (2 mg/mL) and mannitol (50 mg/mL), sterile filtering the solution and filling into sealable 1 mL vials or ampoules.

(iv) Subcutaneous Injection Formulation

A composition for sub-cutaneous administration is prepared by mixing a compound of the formula (1) with pharmaceutical grade corn oil to give a concentration of 5 mg/mL. The composition is sterilised and filled into a suitable container.

EQUIVALENTS

It will readily be apparent that numerous modifications and alterations may be made to the specific embodiments of the invention described above without departing from the principles underlying the invention. All such modifications and alterations are intended to be embraced by this application.

The invention claimed is:
1. A compound of the formula (1):

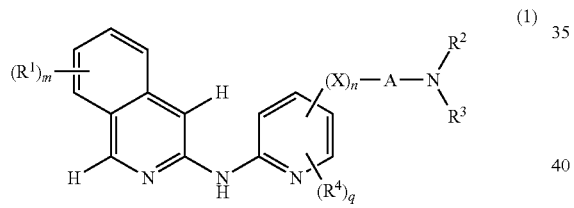

or a salt, solvate, tautomer or N-oxide thereof; wherein
X is O, CO, $X^1C(X^2)$, $C(X^2)X^1$, $X^1C(X^2)X^1$, S, SO, $SO_2$, $NR^C$, $SO_2NR^c$ or $NR^cSO_2$;
m is 0, 1 or 2;
n is 0 or 1;
q is 0, 1 or 2;
A is a straight chain or branched $C_{1-6}$ alkylene group optionally interrupted by O, provided that when n is 1 and X is O, S or $NR^c$, then there are at least two carbon atoms between X and $NR^2R^3$;
$R^1$ is selected from halogen; cyano; nitro; an acyclic $C_{1-6}$ hydrocarbon group optionally substituted by hydroxy or $C_{1-2}$-alkoxy or by one or more fluorine atoms; $C_{3-7}$ cycloalkyl optionally substituted by one or two substituents selected from amino, hydroxy, fluorine, methoxy and methyl; phenyl optionally substituted by one to three substituents $R^7$; five membered heteroaryl groups containing 1-4 heteroatoms selected from O, N and S, and being optionally substituted by one to three substituents $R^7$; a group $NR^2R^3$; a group $R^a$—$R^b$; a group O—$R^b$; and a group $C(O)NR^2R^8$;
$R^4$ is selected from fluorine, chlorine, methyl or cyano;

$R^2$ is selected from hydrogen and $C_{1-4}$ alkyl optionally substituted by hydroxy, $C_{1-2}$ alkoxy, amino, mono- or di-$C_{1-2}$ alkylamino,
$R^3$ is a group $R^a$—$R^b$;
or $NR^2R^3$ forms a 4 to 7 membered non-aromatic heterocyclic ring optionally containing a second heteroatom ring member selected from O, N and S and oxidised forms thereof and being optionally substituted by one or more substituents $R^5$;
$R^a$ is a bond, $C(X^2)$, $C(X^2)X^1$, SO, $SO_2$ or $SO_2NR^c$;
$R^b$ is:
hydrogen; or
a 3 to 7-membered carbocyclic or heterocyclic ring containing up to 4 heteroatoms selected from O, N and S and being optionally substituted by one or more substituents $R^5$; or
a $C_{1-12}$ acyclic hydrocarbon group optionally substituted by one or more substituents selected from hydroxy; oxo; halogen; cyano; nitro; carboxy; amino; $N(R^c)_2$; and 3 to 7-membered carbocyclic or heterocyclic rings containing up to 4 heteroatoms selected from O, N and S and being optionally substituted by one or more substituents $R^5$; and wherein the $C_{1-12}$ acyclic hydrocarbon group may optionally be interrupted by one or two moieties $R^d$;
$R^c$ is hydrogen or a $C_{1-4}$ hydrocarbon group;
$R^d$ is O, CO, $X^1C(X^2)$, $C(X^2)X^1$, $X^1C(X^2)X^1$, S, SO, $SO_2$, $NR^c$, $SO_2NR^c$ or $NR^cSO_2$;
$X^1$ is O, S or $NR^c$;
$X^2$ is =O, =S or =$NR^c$;
$R^5$ is $X^2$; halogen; cyano; nitro; $C_{1-4}$ alkyl; hydroxy-$C_{1-4}$ alkyl; a group $R^d$—$R^e$; or a 3 to 7-membered carbocyclic or heterocyclic ring containing up to 4 heteroatoms selected from O, N and S and being optionally substituted by a group $R^6$;
$R^e$ is:
hydrogen; or
a $C_{1-6}$ acyclic hydrocarbon group optionally substituted by one or more substituents selected from hydroxy; oxo; halogen; cyano; nitro; carboxy; amino; and $N(R^c)_2$; wherein the $C_{1-6}$ acyclic hydrocarbon group may optionally be interrupted by one or two moieties $R^d$; or
a 3 to 7-membered carbocyclic or heterocyclic ring containing up to 4 heteroatoms selected from O, N and S and being optionally substituted by a group $R^6$; and
$R^6$ is selected from halogen, cyano, nitro and a group $R^d$—$R^c$;
$R^7$ is selected from halogen; cyano; $C_{1-4}$ alkoxy optionally substituted with one or more fluorine atoms; $C_{1-4}$ alkyl optionally substituted with hydroxy or $C_{1-2}$-alkoxy or with one or more fluorine atoms; and $C_{3-5}$ cycloalkyl; and
$R^8$ is $R^b$; or $NR^2R^8$ forms a 4 to 7 membered non-aromatic heterocyclic ring optionally containing a second heteroatom ring member selected from O, N and S and oxidised forms thereof and being optionally substituted by one or more substituents $R^5$;
but excluding the compound wherein m, n and q are all 0, A is $CH_2$ and $NR^2R^3$ is a 2-phenylmorpholin-4-yl group.

2. A compound according to claim 1 of the formula (1a):

$$\text{(1a)}$$

or a salt, solvate, tautomer or N-oxide thereof; wherein
- X is O, CO, $X^1C(X^2)$, $C(X^2)X^1$, $X^1C(X^2)X^1$, S, SO, $SO_2$, $NR^c$, $SO_2NR^c$ or $NR^cSO_2$;
- m is 0, 1 or 2;
- n is 0 or 1;
- q is 0, 1 or 2;
- A is a straight chain or branched $C_{1-6}$ alkylene group optionally interrupted by O, provided that when n is 1 and X is O, S or $NR^c$, then there are at least two carbon atoms between X and $NR^2R^3$;
- $R^1$ is selected from halogen; cyano; $C_{1-4}$ alkoxy optionally substituted with one or more fluorine atoms; $C_{1-4}$ alkyl optionally substituted by hydroxy or $C_{1-2}$-alkoxy or by one or more fluorine atoms; $C_{3-5}$ cycloalkyl; phenyl optionally substituted by one to three substituents $R^7$; five membered heteroaryl groups containing 1-4 heteroatoms selected from O, N and S, and being optionally substituted by one to three substituents $R^7$;
- $R^4$ is selected from fluorine, chlorine, methyl or cyano;
- $R^2$ is selected from hydrogen and $C_{1-4}$ alkyl optionally substituted by hydroxy, $C_{1-2}$ alkoxy, amino, mono- or di-$C_{1-2}$ alkylamino,
- $R^3$ is a group $R^a$—$R^b$;
- or $NR^2R^3$ forms a 4 to 7 membered non-aromatic heterocyclic ring optionally containing a second heteroatom ring member selected from O, N and S and oxidised forms thereof and being optionally substituted by one or more substituents $R^5$;
- $R^a$ is a bond, $C(X^2)$, $C(X^2)X^1$, SO, $SO_2$ or $SO_2NR^c$;
- $R^b$ is:
  - hydrogen; or
  - a 3 to 7-membered carbocyclic or heterocyclic ring containing up to 4 heteroatoms selected from O, N and S and being optionally substituted by one or more substituents $R^5$; or
  - a $C_{1-12}$ acyclic hydrocarbon group optionally substituted by one or more substituents selected from hydroxy; oxo; halogen; cyano; nitro; carboxy; amino; $N(R^c)_2$; and 3 to 7-membered carbocyclic or heterocyclic rings containing up to 4 heteroatoms selected from O, N and S and being optionally substituted by one or more substituents $R^5$; and wherein the $C_{1-12}$ acyclic hydrocarbon group may optionally be interrupted by one or two moieties $R^d$; $R^c$ is hydrogen or a $C_{1-4}$ hydrocarbon group;
- $R^d$ is O, CO, $X^1C(X^2)$, $C(X^2)X^1$, $X^1C(X^2)X^1$, S, SO, $SO_2$, $NR^c$, $SO_2NR^c$ or $NR^cSO_2$;
- $X^1$ is O, S or $NR^c$;
- $X^2$ is =O, =S or =$NR^c$;
- $R^5$ is $X^2$; halogen; cyano; nitro; $C_{1-4}$ alkyl; hydroxy-$C_{1-4}$ alkyl; a group $R^d$—$R^e$; or a 3 to 7-membered carbocyclic or heterocyclic ring containing up to 4 heteroatoms selected from O, N and S and being optionally substituted by a group $R^6$;
- $R^e$ is:
  - hydrogen; or
  - a $C_{1-6}$ acyclic hydrocarbon group optionally substituted by one or more substituents selected from hydroxy; oxo; halogen; cyano; nitro; carboxy; amino; and $N(R^c)_2$; wherein the $C_{1-6}$ acyclic hydrocarbon group may optionally be interrupted by one or two moieties $R^d$; or
  - a 3 to 7-membered carbocyclic or heterocyclic ring containing up to 4 heteroatoms selected from O, N and S and being optionally substituted by a group $R^6$; and
- $R^6$ is selected from halogen, cyano, nitro and a group $R^d$—$R^e$; and
- $R^7$ is selected from halogen; cyano; $C_{1-4}$ alkoxy optionally substituted with one or more fluorine atoms; $C_{1-4}$ alkyl optionally substituted with hydroxy or $C_{1-2}$-alkoxy or with one or more fluorine atoms; and $C_{3-5}$ cycloalkyl;

but excluding the compound wherein m, n and q are all 0, A is $CH_2$ and $NR^2R^3$ is a 2-phenylmorpholin-4-yl group.

3. A compound according to claim 1 wherein A is —$CH_2$—, —$CH_2CH_2$—, —$CH_2CH_2CH_2$— or —$CH_2CH_2CH_2CH_2$—.

4. A compound according to claim 1 wherein $R^1$ is selected from halogen; cyano; $C_{1-4}$ alkoxy optionally substituted with one or more fluorine atoms; $C_{1-4}$ alkyl optionally substituted with hydroxy or $C_{1-2}$-alkoxy or with one or more fluorine atoms; $C_{3-4}$ cycloalkyl; and five membered heteroaryl groups containing 1-4 heteroatoms selected from O, N and S and being optionally substituted with one or two methyl groups or halogen atoms.

5. A compound according to claim 4 wherein $R^1$ is selected from chlorine; fluorine; bromine; cyano; $C_{1-3}$ alkyl optionally substituted with hydroxy or methoxy or with one or more fluorine atoms; $C_{1-3}$ alkoxy optionally substituted with one or more fluorine atoms; and five membered heteroaryl groups containing 1-2 heteroatoms selected from O, N and S and being optionally substituted with one or two methyl groups.

6. A compound according to claim 1 wherein q is 0 or 1.

7. A compound according to claim 1 wherein $NR^2R^3$ forms a 4 to 7 membered non-aromatic heterocyclic ring optionally containing a second heteroatom ring member selected from O, N and S and oxidised forms thereof and being optionally substituted by one or more substituents $R^5$ as defined in claim 1.

8. A compound according to claim 7 wherein the non-aromatic heterocyclic ring is selected from 5 and 6-membered rings.

9. A compound according to claim 8 wherein the 5 and 6-membered rings are selected from pyrrolidine, piperidine, piperazine, morpholine and thiomorpholine, each of which may be optionally substituted with one or more substituents $R^5$.

10. A compound according to claim 7 wherein the non-aromatic heterocyclic ring is substituted by 0, 1 or 2 substituents $R^5$.

11. A compound according to claim 10 wherein the non-aromatic heterocyclic ring is unsubstituted or is substituted by 1 substituent $R^5$ selected from hydroxy, $C_{1-4}$ alkyl; hydroxy-$C_{1-4}$ alkyl; $C_{1-4}$ alkanoyl; hydroxy-$C_{1-4}$ alkanoyl; $C_{1-4}$ alkylsulphonyl; carbamoyl; mono-$C_{1-4}$ alkylcarbamoyl and di-$C_{1-4}$ alkylcarbamoyl.

12. A compound according to claim 11 wherein $R^5$ is selected from methylsulphonyl, acetyl, carbamoyl, N-methylcarbamoyl, N,N-dimethylcarbamoyl and hydroxyacetyl.

13. A compound according to claim 1 having the general formula (2):

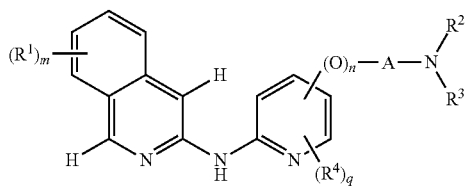

(2)

or a salt, solvate, tautomer or N-oxide thereof wherein m, n, q, $R^1$, $R^2$, $R^3$ and $R^4$ are as defined in claim 1.

14. A compound according to claim 13 having the formula (3):

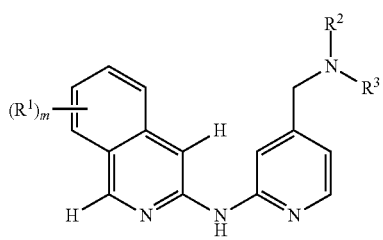

(3)

or a salt, solvate, tautomer or N-oxide thereof.

15. A compound according to claim 14 having the formula (4):

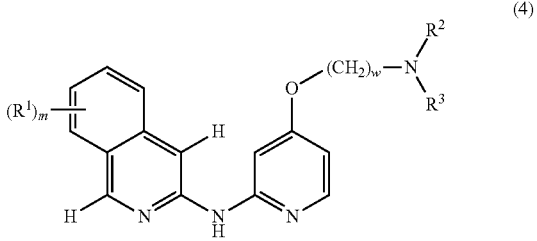

(4)

or a salt, solvate, tautomer or N-oxide thereof; where w is 2 or 3.

16. A compound according to claim 1 wherein $R^2$ is selected from hydrogen, $C_{1-3}$ alkyl, and $C_{2-3}$ alkyl substituted by amino, mono- or dimethylamino; and $R^3$ is selected from hydrogen and $C_{1-4}$ alkyl optionally substituted by hydroxy, $C_{1-2}$ alkoxy, amino, mono- or di-$C_{1-2}$ alkylamino.

17. A pharmaceutical composition comprising a compound as defined in claim 1 and a pharmaceutically acceptable carrier.

* * * * *